(12) United States Patent
Buettelmann et al.

(10) Patent No.: US 8,357,703 B2
(45) Date of Patent: *Jan. 22, 2013

(54) PYRIDINES

(75) Inventors: Bernd Buettelmann, Schopfheim (DE); Roland Jakob-Roetne, Inzlingen (DE); Henner Knust, Rheinfelden (DE); Matthew C. Lucas, Verona, NJ (US); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/772,250

(22) Filed: May 3, 2010

(65) Prior Publication Data

US 2010/0286117 A1  Nov. 11, 2010

(30) Foreign Application Priority Data

May 7, 2009 (EP) .................................. 09159631

(51) Int. Cl.
A61K 31/4427 (2006.01)
C07D 413/12 (2006.01)

(52) U.S. Cl. .................. 514/340; 546/268.1; 546/268.4; 546/272.1; 514/336

(58) Field of Classification Search ............... 546/268.1, 546/268.4, 272.1; 514/336, 340
See application file for complete search history.

(56) References Cited

U.S. PATENT DOCUMENTS

| 4,639,266 A | 1/1987 | Heubach et al. |
| 2003/0055085 A1 | 3/2003 | Wagener et al. |
| 2004/0006226 A1 | 1/2004 | Ladduwahetty et al. |

FOREIGN PATENT DOCUMENTS

| DE | 3525205 | 3/1986 |
| EP | 1894924 | 3/2008 |
| EP | 1894928 | 3/2008 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 02081474 | 10/2002 |
| WO | 03004027 | 1/2003 |
| WO | 03015771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007039389 | 4/2007 |
| WO | 2007052843 | 5/2007 |
| WO | 2007076260 | 7/2007 |
| WO | 2007092751 | 8/2007 |
| WO | 2008025539 | 3/2008 |
| WO | 2008025540 | 3/2008 |
| WO | 2009071476 | 6/2009 |

OTHER PUBLICATIONS

Buettelmann et al (2009): STN International HCAPLUS database, (Columbus, Ohio), Accession No. 2009:675729.*
McNamara et al., Psychobiology (1993), vol. 21, pp. 101-108.
Goodman et al., Tetrahedron (1999) vol. 55 pp. 15067-15070.
Abstract corresponding to JP 2007/230909.
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.

(Continued)

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention is concerned with novel isoxazoles of formula I

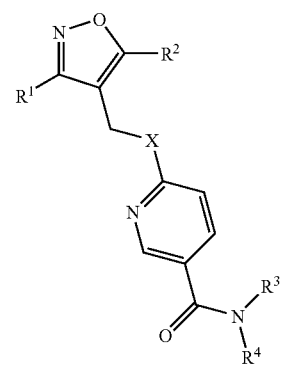

wherein X, $R^1$, $R^2$, $R^3$ and $R^4$ are as described herein, as well as pharmaceutically acceptable salts and esters thereof. The active compounds of the present invention have affinity and selectivity for GABA A α5 receptor. Further the present invention is concerned with the manufacture of the active compounds of formula I, pharmaceutical compositions containing them and their use as therapeutics.

20 Claims, No Drawings

OTHER PUBLICATIONS

Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
Delong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.

* cited by examiner

PYRIDINES

PRIORITY TO RELATED APPLICATION(S)

This application claims the benefit of European Patent Application No. 09159631.2, filed May 7, 2009, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

The present invention provides isoxazole-pyridines having affinity and selectivity for GABA A α5 receptor, their manufacture, pharmaceutical compositions containing them and their use as therapeutics.

In particular, the present invention provides isoxazoles of formula I

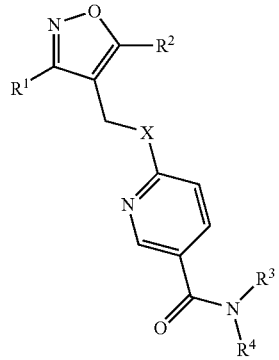

wherein
X is O or NH;
$R^1$ is
  a) lower-alkyl or lower-alkoxy, each optionally substituted with 1, 2, 3 or 4 substituents independently selected from the group consisting of halogen, cyano, hydroxy and lower-alkoxy, or
  b) cycloalkyl or heterocyclyl, each optionally substituted with 1, 2, 3 or 4 substituents independently selected from the group consisting of halogen, cyano, hydroxy, lower-alkyl and lower-alkoxy;
$R^2$ is hydrogen or lower-alkyl optionally substituted with 1, 2, 3 or 4 substituents independently selected from the group consisting of halogen, cyano and lower-alkoxy;
$R^3$ is hydrogen or lower-alkyl optionally substituted with 1, 2, 3 or 4 substituents independently selected from the group consisting of halogen, cyano, hydroxy and lower-alkoxy;
$R^4$ is lower-alkyl, cycloalkyl, heterocyclyl or heteroaryl, each optionally substituted with 1, 2, 3 or 4 substituents independently selected from the group consisting of halogen, cyano, hydroxy, oxo, lower alkyl and lower-alkoxy;
or wherein $R^3$ and $R^4$, together with the nitrogen atom to which they are attached, form a heterocyclyl, optionally substituted with 1, 2, 3 or 4 substituents independently selected from the group consisting of halogen, cyano, hydroxy, lower-alkyl, lower-alkoxy and oxo;
or a pharmaceutically acceptable salt or ester thereof.

DETAILED DESCRIPTION OF THE INVENTION

The present invention provides compounds of formula I and their pharmaceutically acceptable salts and esters and pharmaceutical compositions containing them. The invention also provides methods for the manufacture of the compounds and compositions of the invention. The invention further provides methods for the treatment or prevention of diseases related to the GABA A α5 receptor. The compounds of present invention are preferably inverse agonists of GABA A α5.

The compounds of present invention and their pharmaceutically acceptable salts and esters can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

Unless otherwise indicated, the following definitions are set forth to illustrate and define the meaning and scope of the various terms used to describe the invention herein.

The following definitions of the general terms apply irrespective of whether the terms in question appear alone or in combination.

The nomenclature used in this application is based on AutoNom™ 2000, a Beilstein Institute computerized system for the generation of IUPAC systematic nomenclature. Chemical structures shown herein were prepared using ISIS™/Draw version 2.5. Any open valency appearing on a carbon, oxygen, sulfur or nitrogen atom in the structures herein indicates the presence of a hydrogen atom.

The term "substituted", unless specifically defined otherwise, means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. 1, 2, 3, 4 or 5 substituents are preferred, unless specifically defined otherwise.

The term "halogen" refers to fluorine, chlorine, bromine and iodine, with fluorine being preferred.

The term "lower-alkyl" denotes a saturated straight- or branched-chain group containing from 1 to 7 carbon atoms, for example, methyl, ethyl, propyl, isopropyl, n-butyl, isobutyl, sec-butyl or tert-butyl, as well as those groups specifically illustrated by the examples herein below. Preferred lower-alkyl groups are methyl, propyl, isopropyl, butyl and 1-methyl-butyl. Particularly preferred are methyl, isopropyl and butyl.

The term "lower-alkoxy" denotes a group —O—R wherein R is lower-alkyl as defined above, preferably isobutoxy.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl or cyclohexyl, as well as those groups specifically illustrated by the examples herein below. Preferred cycloalkyls are cyclopropyl, cyclopentyl and cyclohexyl. Particularly preferred is cyclopropyl and cyclohexyl.

The term "heterocyclyl" refers to a monovalent 3 to 7 membered saturated or partly unsaturated monocyclic ring containing one, two or three ring heteroatoms selected from N, O and S. One or two ring heteroatoms are preferred. Preferred are 4 to 6 membered heterocyclyl comprising one or two ring heteroatoms selected from N, O and S. S can optionally be substituted by two oxo groups. Examples for heterocyclyl moieties are pyrrolidinyl, tetrahydro-furanyl, tetrahydro-pyranyl, tetrahydro-thienyl, tetrahydro-pyridinyl, tetrahydro-pyryl, azetidinyl, thiazolidinyl, oxazolidinyl, piperidinyl, morpholinyl, thiomorpholinyl, 1,1-dioxo-thiomorpholin-4-yl, piperazinyl, azepanyl, diazepanyl, oxazepanyl or dihydro-oxazolyl, as well as those groups specifically illustrated by the examples herein below. Among the preferred heterocyclyls are azetidin-1-yl, pyrrolidin-1-yl, tetrahydro-furan-3-yl, tetrahydro-pyran-4-yl and 1,1-dioxo-1,6-thiomorpholin-4-yl. Particularly preferred are pyrrolidin-1-yl, tetrahydro-furan-3-yl and tetrahydro-pyran-4-yl.

The term "aryl" refers to a monovalent aromatic carbocyclic ring system, comprising 6 to 14, preferably 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g. as defined below and in the claims.

The term "heteroaryl" refers to an aromatic 5 to 6 membered monocyclic ring or 9 to 10 membered bicyclic ring which contains 1, 2 or 3 ring atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl or isoquinolinyl, as well as those groups specifically illustrated by the examples herein below. Preferred heteroaryl groups are pyrazol-3-yl and pyrazol-4-yl. Heteroaryl can also be substituted e.g. as defined below and in the claims. Among the preferred heteroaryl substituted by lower-alkyl are 1-methyl-1H-pyrazol-3-yl and 1-methyl-1H-pyrazol-4-yl. Particularly preferred is 1-methyl-1H-pyrazol-4-yl.

The term "lower-alkyl substituted by halogen" refers to lower-alkyl groups as defined above which are mono- or multiply substituted with halogen. Examples of lower-alkyl substituted by halogen groups are e.g. $CFH_2$, $CF_2H$, $CF_3$, $CF_3CH_2$, $CF_3(CH_2)_2$, $(CF_3)_2CH$ or $CF_2H-CF_2$, as well as those groups specifically illustrated by the examples herein below. Among the preferred lower-alkyl substituted by halogen are 2,2,2-trifluoro-ethyl, 2,2,2-trifluoro-1-methyl-ethyl and 3,3,3-trifluoro-propyl.

The term "lower-alkyl substituted by hydroxy" denotes a lower-alkyl group as defined above wherein at least one of the hydrogen atoms of the alkyl group is replaced by a hydroxy group. Examples of lower-alkyl substituted by hydroxy include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one or two hydroxy group. Among the preferred lower-alkyl substituted by hydroxy groups are 2-hydroxy-ethyl, 2-hydroxy-1-methyl-ethyl, 2-hydroxy-1,1-dimethyl-ethyl, 2-hydroxy-1-hydroxymethyl-ethyl, 2-hydroxy-propyl and 2-hydroxy-2-methyl-propyl. Particularly preferred is 2-hydroxy-1-methyl-ethyl.

The term "cycloalkyl substituted by lower-alkyl" denotes a cycloalkyl group as defined above wherein at least one of the hydrogen atoms of the cycloalkyl moiety is replaced by a lower-alkyl group. Examples of cycloalkyl substituted by lower-alkyl include but are not limited to 1-methyl-cyclopropyl, 2-ethyl-cyclopentyl and 3-methyl-cyclohexyl. Among the preferred cycloalkyl substituted by lower-alkyl is 1-methyl-cyclopropyl.

"Pharmaceutically acceptable," such as pharmaceutically acceptable carrier, excipient, etc., means pharmacologically acceptable and substantially non-toxic to the subject to which the particular compound is administered.

Compounds of formula I can form pharmaceutically acceptable acid addition salts. Examples of such pharmaceutically acceptable salts are salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I which comprise an acidic group, such as e.g. a COOH group, can further form salts with bases. Examples of such salts are alkaline, earth-alkaline and ammonium salts such as e.g. Na—, K—, Ca— and trimethylammonium salt. The term "pharmaceutically acceptable salts" also refers to such salts.

The term "pharmaceutically acceptable esters" embraces derivatives of the compounds of formula I, in which a carboxy group has been converted to an ester. Lower-alkyl, lower-alkyl substituted by hydroxy, lower-alkyl substituted by lower-alkoxy, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aryl-lower-alkyl esters are examples of suitable esters. The methyl, ethyl, propyl, butyl and benzyl esters are preferred esters. The term "pharmaceutically acceptable esters" furthermore embraces compounds of formula I in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention provides compounds of formula I

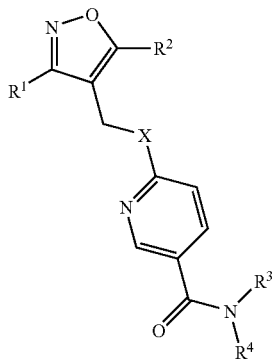

I wherein
X is O or NH;
R$^1$ is
  a) lower-alkyl or lower-alkoxy, each optionally substituted with 1, 2, 3 or 4 substituents independently selected from the group consisting of halogen, cyano, hydroxy and lower-alkoxy, or
  b) cycloalkyl or heterocyclyl, each optionally substituted with 1, 2, 3 or 4 substituents independently selected from the group consisting of halogen, cyano, hydroxy, lower-alkyl and lower-alkoxy;
R$^2$ is hydrogen or lower-alkyl optionally substituted with 1, 2, 3 or 4 substituents independently selected from the group consisting of halogen, cyano and lower-alkoxy;
R$^3$ is hydrogen or lower-alkyl optionally substituted with 1, 2, 3 or 4 substituents independently selected from the group consisting of halogen, cyano, hydroxy and lower-alkoxy;
R$^4$ is lower-alkyl, cycloalkyl, heterocyclyl or heteroaryl, each optionally substituted with 1, 2, 3 or 4 substituents independently selected from the group consisting of halogen, cyano, hydroxy, oxo, lower alkyl and lower-alkoxy;
or wherein R$^3$ and R$^4$, together with the nitrogen atom to which they are attached, form a heterocyclyl, optionally substituted with 1, 2, 3 or 4 substituents independently selected from the group consisting of halogen, cyano, hydroxy, lower-alkyl, lower-alkoxy and oxo;
and pharmaceutically acceptable salts and esters thereof.

Compounds of formula I are individually preferred and pharmaceutically acceptable salts thereof are individually preferred and pharmaceutically acceptable esters thereof are individually preferred, with the compounds of formula I being particularly preferred.

The compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemate, by asymmetric synthesis or asymmetric chromatography (chromatography with a chiral adsorbents or eluant). The invention embraces all of these forms.

Further, it is to be understood that every embodiment relating to a specific residue R$^1$ to R$^4$ as disclosed herein can be combined with any other embodiment relating to another residue R$^1$ to R$^4$ as disclosed herein.

Further, the present invention relates to compounds of formula I, wherein
X is O or NH;
R$^1$ is
  a) lower-alkyl or lower-alkoxy, each optionally substituted with 1, 2, 3 or 4 substituents independently selected from the group consisting of halogen, cyano, hydroxy and lower-alkoxy, or
  b) cycloalkyl or heterocyclyl, each optionally substituted with 1, 2, 3 or 4 substituents independently selected from the group consisting of halogen, cyano, hydroxy, lower-alkyl and lower-alkoxy;
R$^2$ is hydrogen or lower-alkyl optionally substituted with 1, 2, 3 or 4 substituents independently selected from the group consisting of halogen, cyano and lower-alkoxy;
R$^3$ is hydrogen or lower-alkyl optionally substituted with 1, 2, 3 or 4 substituents independently selected from the group consisting of halogen, cyano, hydroxy and lower-alkoxy;
R$^4$ is lower-alkyl, cycloalkyl, heterocyclyl or heteroaryl, each optionally substituted with 1, 2, 3 or 4 substituents independently selected from the group consisting of halogen, cyano, hydroxy, and lower-alkoxy;
or wherein R$^3$ and R$^4$, together with the nitrogen atom to which they are attached, form a heterocyclyl, optionally substituted with 1, 2, 3 or 4 substituents independently selected from the group consisting of halogen, cyano, hydroxy, lower-alkyl, lower-alkoxy and oxo;
and pharmaceutically acceptable salts and esters thereof.

In certain embodiments of the compound of formula I, X is preferably O.

In certain embodiments of the compound of formula I, $R^1$ is lower-alkyl, lower-alkyl substituted by halogen, cycloalkyl, lower-alkoxy or heterocyclyl. Even more preferred compounds of the present invention are those, wherein $R^1$ is lower-alkyl, cycloalkyl, lower-alkoxy or pyrrolidinyl. Most preferred are compounds wherein $R^1$ is butyl, cyclohexyl, isobutoxy or pyrrolidin-1-yl.

In certain embodiments of the compound of formula I, $R^2$ is hydrogen or lower-alkyl, preferably lower-alkyl. Even more preferred compounds of the present invention are those, wherein $R^2$ is methyl.

In certain embodiments of the compound of formula I, $R^3$ is preferably hydrogen.

In certain embodiments of the compound of formula I, $R^4$ is preferably lower-alkyl, lower-alkyl substituted by halogen, lower-alkyl substituted by hydroxy, cycloalkyl, cycloalkyl substituted by lower-alkyl, heterocyclyl or heteroaryl substituted by lower-alkyl. Even more preferred compounds of the present invention are those, wherein $R^4$ is lower-alkyl, lower-alkyl substituted by hydroxy, cycloalkyl, tetrahydro-furanyl, tetrahydro-pyranyl or pyrazolyl substituted by lower-alkyl. Most preferred are compounds wherein $R^4$ is isopropyl, 2-hydroxy-1-methyl-ethyl, (S)-2-hydroxy-1-methyl-ethyl, cyclopropyl, tetrahydro-furan-3-yl, tetrahydro-pyran-4-yl or 1-methyl-1H-pyrazol-4-yl.

In certain embodiments of the compound of formula I, $R^3$ and $R^4$, together with the nitrogen atom to which they are attached, preferably form a heterocyclyl. Even more preferred compounds of the present invention are those, wherein $R^3$ and $R^4$, together with the nitrogen atom to which they are attached, form azetidin-1-yl or 1,1-dioxo-1,6-thiomorpholin-4-yl.

If $R^3$ and $R^4$, together with the nitrogen atom to which they are attached, form a heterocyclyl, they then preferably form azetidin-1-yl or 1,1-dioxo-1,6-thiomorpholin-4-yl.

In particular, preferred compounds are the compounds of formula I described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Particularly preferred compounds of formula I of present invention are those selected from the group consisting of:

N-Isopropyl-6-((5-methyl-3-propyl-isoxazol-4-yl)methoxy)-nicotinamide,
6-((5-Methyl-3-propyl-isoxazol-4-yl)methoxy)-N-(tetrahydro-pyran-4-yl)-nicotinamide,
N-Isopropyl-6-[(5-methyl-3-(3,3,3-trifluoro-propyl)-isoxazol-4-yl)methoxy]-nicotinamide,
6-[(5-Methyl-3-(3,3,3-trifluoro-propyl)-isoxazol-4-yl)methoxy]-N-(tetrahydro-pyran-4-yl)-nicotinamide,
6-((3-Butyl-5-methyl-isoxazol-4-yl)methoxy)-N-isopropyl-nicotinamide,
6-((3-Butyl-5-methyl-isoxazol-4-yl)methoxy)-N-cyclopropyl-nicotinamide,
6-((3-Butyl-5-methyl-isoxazol-4-yl)methoxy)-N-(tetrahydro-pyran-4-yl)-nicotinamide,
6-((3-Butyl-5-methyl-isoxazol-4-yl)methoxy)-N-(2-hydroxy-1,1-dimethyl-ethyl)-nicotinamide,
6-((3-Butyl-5-methyl-isoxazol-4-yl)methoxy)-N-(2-hydroxy-1-methyl-ethyl)-nicotinamide,
6-((3-Butyl-5-methyl-isoxazol-4-yl)methoxy)-N-(2-hydroxy-ethyl)-nicotinamide,
6-((3-Butyl-5-methyl-isoxazol-4-yl)methoxy)-N—((R)-2-hydroxy-1-methyl-ethyl)-nicotinamide,
6-((3-Butyl-5-methyl-isoxazol-4-yl)methoxy)-N—((S)-2-hydroxy-1-methyl-ethyl)-nicotinamide,
6-((3-Butyl-5-methyl-isoxazol-4-yl)methoxy)-N-(2-hydroxy-2-methyl-propyl)-nicotinamide,
6-((3-Butyl-5-methyl-isoxazol-4-yl)methoxy)-N-(tetrahydro-furan-3-yl)-nicotinamide,
6-((3-Butyl-5-methyl-isoxazol-4-yl)methoxy)-N-(2-hydroxy-1-hydroxymethyl-ethyl)-nicotinamide,
6-((3-Butyl-5-methyl-isoxazol-4-yl)methoxy)-N-(S)-tetrahydro-furan-3-yl-nicotinamide,
6-((3-Butyl-5-methyl-isoxazol-4-yl)methoxy)-N-(2-hydroxy-propyl)-nicotinamide,
[6-((3-Butyl-5-methyl-isoxazol-4-yl)methoxy)-pyridin-3-yl]-(1,1-dioxo-1,6-thiomorpholin-4-yl)-methanone,
6-((3-Butyl-5-methyl-isoxazol-4-yl)methoxy)-N-(S)-2,2,2-trifluoro-1-methyl-ethyl)-nicotinamide,
6-((3-Butyl-5-methyl-isoxazol-4-yl)methoxy)-N-(1-methyl-cyclopropyl)-nicotinamide,
Azetidin-1-yl-[6-((3-butyl-5-methyl-isoxazol-4-yl)methoxy)-pyridin-3-yl]-methanone,
6-((3-Butyl-5-methyl-isoxazol-4-yl)methoxy)-N-(1-methyl-1H-pyrazol-4-yl)-nicotinamide,
6-((3-Butyl-5-methyl-isoxazol-4-yl)methoxy)-N-(1-methyl-1H-pyrazol-3-yl)-nicotinamide,
6-((3-Butyl-isoxazol-4-yl)methoxy)-N-isopropyl-nicotinamide,
6-((3-Butyl-isoxazol-4-yl)methoxy)-N-(2,2,2-trifluoro-ethyl)-nicotinamide,
6-((3-Butyl-isoxazol-4-yl)methoxy)-N-(tetrahydro-pyran-4-yl)-nicotinamide,
6-((3-Butyl-isoxazol-4-yl)methoxy)-N—((S)-2-hydroxy-1-methyl-ethyl)-nicotinamide,
N-Isopropyl-6-[(5-methyl-3-(1-methyl-butyl)-isoxazol-4-yl)methoxy]-nicotinamide,
6-((3-Cyclopentyl-5-methyl-isoxazol-4-yl)methoxy)-N-isopropyl-nicotinamide,
6-((3-Cyclohexyl-5-methyl-isoxazol-4-yl)methoxy)-N-isopropyl-nicotinamide,
6-((3-Cyclohexyl-5-methyl-isoxazol-4-yl)methoxy)-N-cyclopropyl-nicotinamide,
6-((3-Cyclohexyl-5-methyl-isoxazol-4-yl)methoxy)-N-(tetrahydro-pyran-4-yl)-nicotinamide,
6-((3-Cyclohexyl-5-methyl-isoxazol-4-yl)methoxy)-N-(2-hydroxy-ethyl)-nicotinamide,
6-((3-Cyclohexyl-5-methyl-isoxazol-4-yl)methoxy)-N-(2-hydroxy-1,1-dimethyl-ethyl)-nicotinamide,
6-((3-Cyclohexyl-5-methyl-isoxazol-4-yl)methoxy)-N-(2-hydroxy-1-methyl-ethyl)-nicotinamide,
N-Isopropyl-6-[(5-methyl-3-(tetrahydro-pyran-4-yl)-isoxazol-4-yl)methoxy]-nicotinamide,
N—((S)-2-Hydroxy-1-methyl-ethyl)-6-[(5-methyl-3-(tetrahydro-pyran-4-yl)-isoxazol-4-yl)methoxy]-nicotinamide,
6-((3-Isobutoxy-5-methyl-isoxazol-4-yl)methoxy)-N-isopropyl-nicotinamide,
N-Isopropyl-6-((5-methyl-3-pyrrolidin-1-yl-isoxazol-4-yl)methoxy)-nicotinamide,
N-Isopropyl-6-((5-methyl-3-pyrrolidin-1-yl-isoxazol-4-yl)methoxy)-nicotinamide,
6-[((3-Butyl-5-methyl-isoxazol-4-yl)methyl)-amino]-N-isopropyl-nicotinamide,
6-[((3-Butyl-5-methyl-isoxazol-4-yl)methyl)-amino]-N-(2-hydroxy-1-methyl-ethyl)-nicotinamide, and
6-[((3-Butyl-5-methyl-isoxazol-4-yl)methyl)-amino]-N-(tetrahydro-pyran-4-yl)-nicotinamide,
and pharmaceutically acceptable salts and esters thereof.

Even more preferred compounds of formula I of present invention are those selected from the group consisting of:
6-((3-Butyl-5-methyl-isoxazol-4-yl)methoxy)-N-isopropyl-nicotinamide,
6-((3-Butyl-5-methyl-isoxazol-4-yl)methoxy)-N-(2-hydroxy-1-methyl-ethyl)-nicotinamide,
6-((3-Butyl-5-methyl-isoxazol-4-yl)methoxy)-N-(S)-2-hydroxy-1-methyl-ethyl)-nicotinamide,
6-((3-Butyl-5-methyl-isoxazol-4-yl)methoxy)-N-(tetrahydro-furan-3-yl)-nicotinamide,
6-((3-Butyl-5-methyl-isoxazol-4-yl)methoxy)-N-(1-methyl-1H-pyrazol-4-yl)-nicotinamide,
6-((3-Cyclohexyl-5-methyl-isoxazol-4-yl)methoxy)-N-isopropyl-nicotinamide,
6-((3-Cyclohexyl-5-methyl-isoxazol-4-yl)methoxy)-N-cyclopropyl-nicotinamide,
6-((3-Cyclohexyl-5-methyl-isoxazol-4-yl)methoxy)-N-(2-hydroxy-1-methyl-ethyl)-nicotinamide,
6-((3-Isobutoxy-5-methyl-isoxazol-4-yl)methoxy)-N-isopropyl-nicotinamide,
N-Isopropyl-6-((5-methyl-3-pyrrolidin-1-yl-isoxazol-4-yl)methoxy)-nicotinamide, and
N-Isopropyl-6-((5-methyl-3-pyrrolidin-1-yl-isoxazol-4-yl)methoxy)-nicotinamide,
and pharmaceutically acceptable salts and esters thereof.

The invention further provides a process for the manufacture of compounds of formula I as defined above, which process comprises:
a) reacting a compound of formula II:

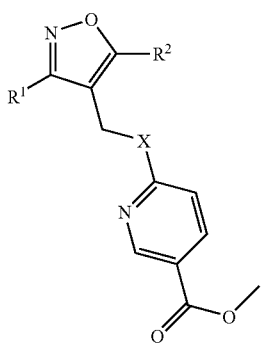

II with NHR$^3$R$^4$, or
b) reacting a compound of formula III:

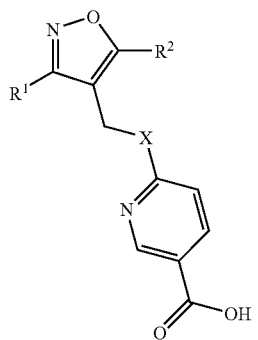

III with NHR$^3$R$^4$, or
c) saponification of a compound of formula II to a compound of formula III followed by reaction with NHR$^3$R$^4$,
wherein X, R$^1$, R$^2$, R$^3$ and R$^4$ are as defined above.

The reaction of a compound of formula II with NHR$^3$R$^4$ to a compound of formula I can be carried out under conditions as described in the examples or under conditions well known to the person skilled in the art. For example, the reaction can be performed in the presence of trimethylaluminium in a suitable solvent like dioxane at elevated temperatures e.g. at 85-95° C.

Alternatively, the reaction can be performed in the presence of 1,5,7-triazabicyclo[4.4.0]dec-5-ene in a suitable solvent like toluene at elevated temperatures e.g. at 50° C.

The reaction of a compound of formula III with NHR$^3$R$^4$ to a compound of formula I can be carried out under conditions as described in the examples or under conditions well known to the person skilled in the art. For example, the reaction can be performed in the presence of Hünigs Base (N,N-diisopropylethylamine) and O-(benzotriazol-1-yl)-N,N,N',N'-tetramethyluronium tetrafluoroborate in a suitable solvent like dimethylformamide at room temperature. Alternatively, the reaction can be performed in the presence of 1,1'-carbonyldiimidazole in a suitable solvent like dimethylformamide at elevated temperatures e.g. at 80° C. Furthermore, the reaction can be performed in the presence of 1-ethyl-3-(3-dimethylaminopropyl) carbodiimide hydrochloride, N1-hydroxybenzotriazole and Hünigs Base (N,N-diisopropylethylamine) in a suitable solvent like dichloromethane at room temperature.

The saponification of a compound of formula II to a compound of formula III can be carried out under conditions as described in the examples or under conditions well known to the person skilled in the art. For example, the reaction can be performed in the presence of sodiumhydroxide in a suitable solvent like water at room temperature. Alternatively, the reaction can be performed in the presence of lithiumhydroxide in a suitable solvent like methanol, tetrahydrofuran or water at room temperature.

The present invention also relates to compounds of formula I as defined above, when prepared by a process as described above.

The present compounds of formula I and their pharmaceutically acceptable salts can be prepared by a process comprising the steps of:
a) reacting a compound of formula 1:

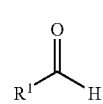

1 with hydroxylamine hydrochloride in a suitable solvent, such as ethanol and water in the presence of a base, such as aqueous sodium hydroxide to give a compound of formula 2:

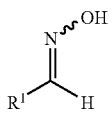

2 b) followed by reacting the compound of formula 2 with a chlorinating agent such as N-chlorosuccinimide in a suitable solvent, such as DMF to give a compound of formula 3:

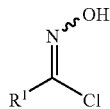

3 c) and then either reacting the compound of formula 3 with a compound of formula 4:

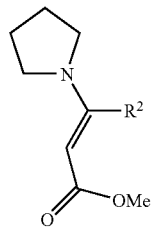

4 in the presence of a suitable base, such as triethylamine, in a suitable solvent, such as chloroform, to give a compound of formula 7:

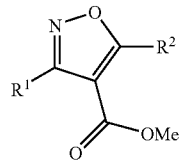

7 d) or alternatively reacting the compound of formula 3 with a compound of formula 5:

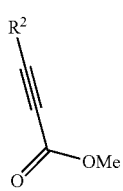

5 in the presence of a suitable base, such as triethylamine, in a suitable solvent, such as diethylether, to give a compound of formula 7;

e) or alternatively reacting the compound of formula 3 with a compound of formula 6:

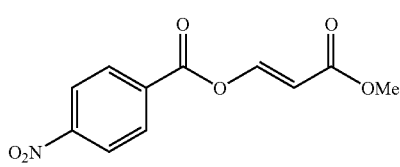

6 in the presence of a suitable base, such as triethylamine, in a suitable solvent, such as DCM, to give a compound of formula 7;

f) The compound of formula 7 can be reacted with a reducing agent, such as lithiumaluminiumhydride, in a suitable solvent, such as THF to give a compound of formula 8:

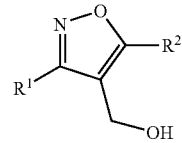

8 g) or alternatively a compound of formula 7 can be reacted with a hydrolytic agent such as NaOH or LiOH in a suitable solvent such as THF, MeOH or EtOH, water to give a compound of formula 9:

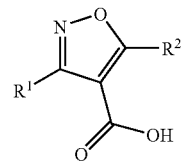

9 h) followed by reacting a compound of formula 9 with a reducing agent, such as lithiumaluminiumhydride or ethylchloroformate in the presence of sodiumborohydride in a suitable solvent such as THF or water to give a compound of formula 8;

i) Compounds of formula 8 can be reacted with a compound of formula 10:

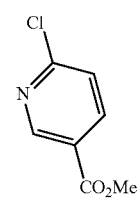

10 in the presence of a suitable base, such as sodium hydride, in a suitable solvent, such as THF to give a compound of formula II-A:

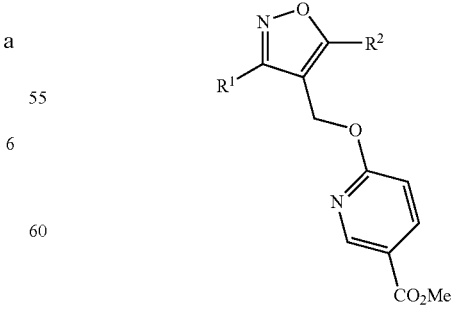

II-A j) Alternatively a compound of formula 8 can be reacted with thionyl chloride in a suitable solvent, such as DCM, to give a compound of formula 11:

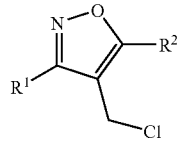

11 k) followed by reacting a compound of formula 11 with phthalimide potassium in a suitable solvent, such as DMF, to give a compound of formula 12:

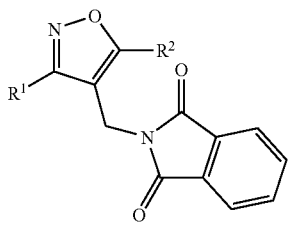

12 l) and then reacting a compound of formula 12 with hydrazine hydrate in a suitable solvent, such as MeOH, to give a compound of formula 13:

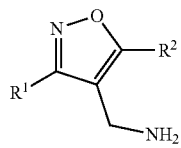

13 m) The compound of formula 13 can be reacted with a compound of formula 10:

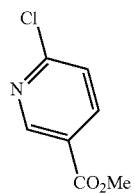

10 in the presence of a suitable base, such as DIPEA, in a suitable solvent, such as DMSO, to give a compound of formula II-B:

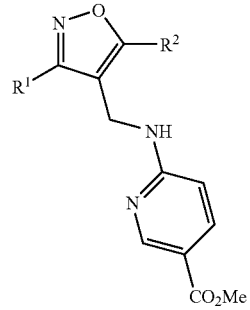

II-B n) Alternatively a compound of formula 14:

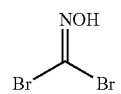

14 can be reacted with ethyl 2-pentynoate in the presence of a suitable base, such as potassium carbonate in a suitable solvent such as DCM to give a compound of formula 15:

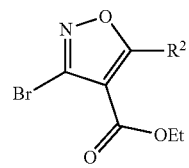

15 o) followed by treatment of the compound of formula 15 with a suitable base, such as BEMP, with a nucleophilic amine such as pyrrolidine at elevated temperatures such as 180° C. in a microwave oven to give a compound of formula 16:

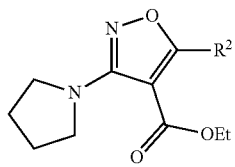

16 p) The compound of formula 16 can be reacted with a reducing agent, such as lithiumaluminiumhydride, in a suitable solvent, such as THF to give a compound of formula 17:

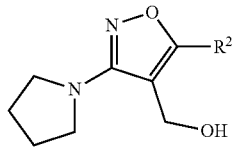

17 q) Compounds of formula 17 can be reacted with a compound of formula 10 in the presence of a suitable base, such as sodium hydride, in a suitable solvent, such as THF to give a compound of formula II-A.

In accordance with Scheme 1, compounds of formula I can be prepared following standard methods.

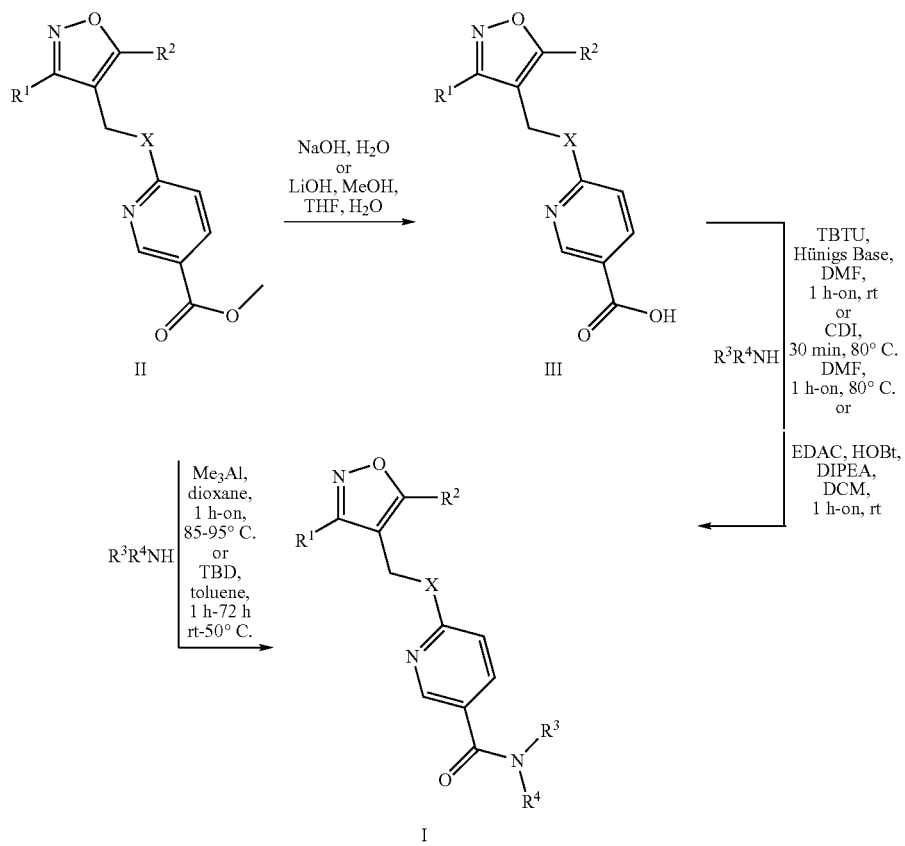

Scheme 1 wherein X, $R^1$, $R^2$, $R^3$ and $R^4$ are as defined above.
BEMP=2-tert-butylimino-2-diethylamino-1,3-dimethylperhydro-1,3,2-diazaphosphorine
CDI=1,1'-carbonyldiimidazole
DCM=dichloromethane
DMAP=N,N-dimethylamino-4-pyridine
DIPEA=N,N-diisopropylethylamine (Hünigs Base)
DMF=dimethylformamide
DMSO=dimethylsulfoxide
EDAC=1-ethyl-3-(3-dimethylaminopropyl) carbodiimide hydrochloride
EtOH=ethanol
HOBt=N1-hydroxybenzotriazole
$Me_3Al$=trimethylaluminium
MeOH=methanol
on=overnight
rt=room temperature
TBD=1,5,7-triazabicyclo[4.4.0]dec-5-ene
TBTU=O-(benzotriazol-1-yl)-N,N,N',N'-tetramethyluronium tetrafluoroborate
TBDMS=tert-butyldimethylsilyl The corresponding salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula I into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula I as well as all intermediate products can be prepared according to analogous methods or according to the methods set forth above. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

As described above, the novel compounds of the present invention and their pharmaceutically acceptable salts and esters possess valuable pharmacological properties and are ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another preferred embodiment, the invention relates to a method for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

The treatment or prevention of cognitive disorders, Alzheimer's disease, schizophrenia, positive, negative and/or cognitive symptoms associated with schizophrenia, Down syndrome, and neurofibromatosis type I, is preferred.

Particularly preferred is the treatment or prevention of Alzheimer's disease.

Particularly preferred is the treatment or prevention of Down syndrome.

Particularly preferred is the treatment or prevention of neurofibromatosis type I.

The compounds were investigated in accordance with the test given hereinafter:

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]flumazenil at a concentration of 1 nM for α1, α2, α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of [$^3$H]flumazenil from α5 subunits of the rat GABA A receptor of 100 nM or less. Most preferred are compounds with a $K_i$ (nM)<35. In a preferred embodiment the compounds of the invention are binding selective for the α5 subunit relative to the α1, α2 and α3 subunit.

Representative test results, obtained by the above described assay measuring binding affinity to HEK293 cells expressing human (h) receptors, are shown in table 1 below.

TABLE 1

Binding affinities to HEK293 cells expressing human (h) receptors of representative examples

| Example | hK$_i$ GABA Aα5 [nM] |
|---|---|
| 1 | 46 |
| 2 | 50.8 |
| 3 | 49 |
| 4 | 39.9 |
| 5 | 4.1 |
| 6 | 6.5 |
| 7 | 5.2 |
| 8 | 15.2 |
| 9 | 3.1 |
| 10 | 5.7 |
| 11 | 7.3 |
| 12 | 3.8 |
| 13 | 9.2 |
| 14 | 5 |
| 15 | 5.7 |
| 16 | 6.5 |
| 17 | 5.2 |
| 18 | 21.1 |
| 19 | 8.4 |
| 20 | 7.5 |
| 21 | 11.5 |
| 22 | 34.5 |
| 23 | 2.2 |
| 24 | 10.7 |
| 25 | 41.1 |
| 26 | 44.9 |
| 27 | 51.9 |
| 28 | 36.1 |
| 29 | 70.9 |
| 30 | 37.6 |
| 31 | 4.3 |
| 32 | 4.7 |
| 33 | 5.2 |
| 34 | 5.8 |
| 35 | 20.3 |
| 36 | 3.7 |
| 37 | 21.9 |
| 38 | 41.6 |
| 39 | 4.7 |
| 40 | 4 |
| 41 | 3.9 |
| 42 | 57.9 |
| 43 | 77 |
| 44 | 67.6 |

The invention also provides pharmaceutical compositions containing compounds of formula I and pharmaceutically acceptable salts and esters thereof with a pharmaceutically acceptable carrier. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragés and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.1 to 1000 mg per person of a compound of formula I should be appropriate, although the above upper limit can also be exceeded when necessary.

The following examples illustrate the present invention without limiting it. All temperatures are given in degrees Celsius.

Example A

Tablets of the following composition are manufactured in the usual manner:

TABLE 2

| possible tablet composition | |
|---|---|
| ingredient | Mg/tablet |
| Active substance | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Example B

Capsules of the following composition are manufactured:

TABLE 3

| possible capsule composition | |
|---|---|
| ingredient | mg/capsule |
| Active substance | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

TABLE 4

| possible suppository composition | |
|---|---|
| ingredient | mg/supp. |
| Active substance | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1 to 44 are provided for illustration of the invention. They should not be considered as limiting the scope of the invention, but merely as being representative thereof.

Example 1

N-Isopropyl-6-((5-methyl-3-propyl-isoxazol-4-yl) methoxy)-nicotinamide

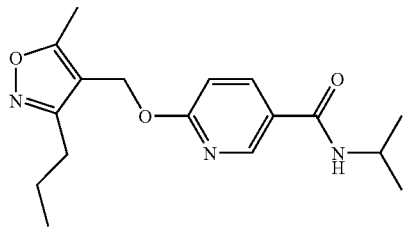 [SMILES: CCCc1noc(C)c1COc1ccc(C(=O)NC(C)C)cn1]

a) (E and/or Z)-Butyraldehyde oxime

To a stirred solution of butyraldehyde (10.0 g, 139 mmol) and hydroxylamine hydrochloride (10.6 g, 153 mmol) in ethanol (225 mL) and water (450 mL) at 2° C. was added NaOH (50% solution in water, 20 mL) dropwise, then the ice-bath was removed and the reaction mixture warmed to room temperature overnight. The reaction mixture was acidified to pH 6 with HCl (6 N) then was extracted with dichloromethane. The combined organic extracts were dried overs sodium sulphate, filtered and concentrated to give the title compound (12.0 g, 99%) as a colourless liquid that was used directly without further purification.

b) 5-Methyl-3-propyl-isoxazole-4-carboxylic acid ethyl ester

To a suspension of N-chlorosuccinimide (18.4 g, 138 mmol) in chloroform (250 mL) at room temperature was added pyridine (1.09 g, 13.8 mmol) and then a solution of (E and/or Z)-butyraldehyde oxime (12.0 g, 138 mmol) in chloroform (260 mL) added dropwise over 20 min. The reaction mixture was stirred at 50° C. for 1.5 h then cooled to room temperature and a solution of ethyl (E)-3-(1-pyrrolidino)-2-butenoate (25.2 g, 138 mmol) in chloroform (120 mL) added dropwise. The reaction mixture was warmed to 50° C. and a solution of triethylamine (13.9 g, 138 mmol) in chloroform (120 mL) added dropwise. After 15 h the reaction mixture was cooled and extracted with water then citric acid (10% w/w aqueous solution). The combined aqueous phases were extracted with dichloromethane, then the combined organic phases were dried, filtered over sodium sulphate, filtered, concentrated then purified by chromatography (silica, 0 to 20% ethyl acetate in heptane) to give the title compound (13.8 g, 51%) as a pale yellow liquid. MS: m/e=232.2 [M+H]+.

c) (5-Methyl-3-propyl-isoxazol-4-yl)-methanol

To a stirred solution of 5-methyl-3-propyl-isoxazole-4-carboxylic acid ethyl ester (13.8 g, 70 mmol) in THF (140 mL) under argon and at 0° C. was added lithium aluminium hydride (3.05 g, 80 mmol) in five portions. After 90 min the reaction mixture was quenched dropwise with Seignette salt solution. The reaction mixture was filtered and the filtrate extracted with ethyl acetate. The combined organic extracts were washed with Seignette salt solution then dried over sodium sulfate, filtered, concentrated and purified by chromatography (silica, 0 to 60% ethyl acetate in heptane) to give the title compound (8.7 g, 80%) as a yellow liquid. MS: m/e=232.2 [M+H]+.

d) 6-(5-Methyl-3-propyl-isoxazol-4-ylmethoxy)-nicotinic acid methyl ester

To a stirred suspension of sodium hydride (2.78 g of a 60% dispersion in mineral oil, 64 mmol) in THF (40 mL) at 0° C. and under argon was added solution of (5-methyl-3-propyl-isoxazol-4-yl)-methanol (7.60 g, 49 mmol) in tetrahydrofuran (40 mL) dropwise. The mixture was warmed to ambient temperature, stirred for 30 min, then cooled to 0° C. and a solution of methyl 6-chloronicotinate (8.40 g, 49 mmol) in THF (40 mL) was added dropwise. The reaction mixture was warmed to room temperature. After 2 h, water was added then the resulting mixture extracted with ethyl acetate. The combined organic extracts were dried, filtered and concentrated. Purification by chromatography (silica, 0 to 20% ethyl acetate in heptane) gave the title compound (8.4 g, 50%) as a light yellow oil. MS: m/e=413.2 [M+H]+.

e) N-Isopropyl-6-(5-methyl-3-propyl-isoxazol-4-ylmethoxy)-nicotinamide

A mixture of 6-(5-methyl-3-propyl-isoxazol-4-ylmethoxy)-nicotinic acid methyl ester (290 mg, 1.0 mmol), isopropylamine (71 mg, 1.2 mmol) and TBD (42 mg, 0.30 mmol) was stirred for 15 h at ambient temperature under argon. The reaction mixture was concentrated onto silica then purified by chromatography (silica, 0 to 60% ethyl acetate in heptane) to give the title compound (95 mg, 30%) as a white solid after trituration with diisopropyl ether. MS: m/e=318.1 [M+H]+.

Example 2

6-((5-Methyl-3-propyl-isoxazol-4-yl)methoxy)-N-(tetrahydro-pyran-4-yl)-nicotinamide

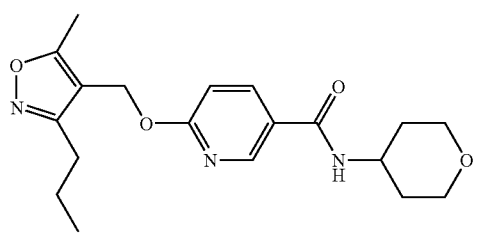 [SMILES: CCCc1noc(C)c1COc1ccc(C(=O)NC2CCOCC2)cn1]

As described for example 1e, 6-(5-methyl-3-propyl-isoxazol-4-ylmethoxy)-nicotinic acid methyl ester (145 mg, 0.50 mmol) was converted, using 4-aminotetrahydropyran instead of isopropylamine, to the title compound (35 mg, 19%) which was obtained as a white solid after purification by chromatography (silica, 0-6% methanol in dichloromethane) and after trituration with diisopropyl ether. MS: m/e=360.3 [M+H]+.

Example 3

N-Isopropyl-6-[(5-methyl-3-(3,3,3-trifluoro-propyl)-isoxazol-4-yl)methoxy]-nicotinamide

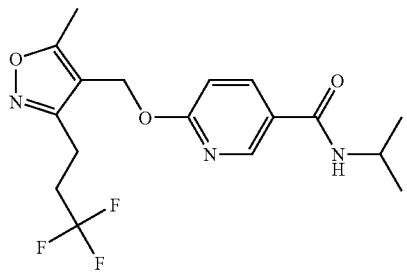 [SMILES: Cc1onc(CCC(F)(F)F)c1COc1ccc(C(=O)NC(C)C)cn1]

a) (E and/or Z)-4,4,4-Trifluoro-butyraldehyde oxime

As described for example 1a 4,4,4-trifluoro-butyraldehyde (9.8 g, 77.7 mmol) instead of butyraldehyde, the title compound (10.6 g, 97%) was obtained as a yellow liquid and as a mixture of cis and trans isomers that was used directly without further purification.

b) 5-Methyl-3-(3,3,3-trifluoro-propyl)-isoxazole-4-carboxylic acid ethyl ester As described for example 1b, (E and/or Z)-4,4,4-trifluoro-butyraldehyde oxime (10.6 g, 75.1 mmol) instead of (E and/or Z)-butanal oxime, the title compound (9.95 g, 53%) was obtained as a yellow liquid after purification by chromatography (silica, 0 to 30% ethyl acetate in heptane). MS: m/e=252.3 [M+H]+.

c) [5-Methyl-3-(3,3,3-trifluoro-propyl)-isoxazol-4-yl]-methanol

As described for example 1c, 5-methyl-3-(3,3,3-trifluoro-propyl)-isoxazole-4-carboxylic acid ethyl ester (9.85 g, 39.2 mmol) instead of 3-propyl-5-methyl-isoxazole-4-carboxylic acid ethyl ester, the title compound (7.87 g, 96%) was obtained as a yellow oil after purification by chromatography (silica, 0 to 80% ethyl acetate in heptane). MS: m/e=210.1 [M+H]+.

d) 6-[5-Methyl-3-(3,3,3-trifluoro-propyl)-isoxazol-4-ylmethoxy]-nicotinic acid methyl ester As described for example 1d, [5-methyl-3-(3,3,3-trifluoro-propyl)-isoxazol-4-yl]-methanol (2.0 g, 9.6 mmol) instead of (3-propyl-5-methyl-isoxazol-4-yl)-methanol, the title compound (0.86 g, 26%) was obtained as a colourless oil after purification by chromatography (silica, 0 to 60% ethyl acetate in heptane). MS: m/e=345.1 [M+H]+.

e) N-Isopropyl-6-[5-methyl-3-(3,3,3-trifluoro-propyl)-isoxazol-4-ylmethoxy]-nicotinamide Trimethylaluminium (1.22 mL of a 2 M solution in toluene, 2.44 mmol) was added dropwise to a stirred solution of isopropylamine (144 mg, 2.46 mmol) in dioxane (4 mL) at room temperature and under argon. After 1 h, a solution of 6-[5-methyl-3-(3,3,3-trifluoro-propyl)-isoxazol-4-ylmethoxy]-nicotinic acid methyl ester (210 mg, 0.61 mmol) in dioxane (4 mL) was added and the reaction mixture warmed to 90° C. After 10 h the reaction mixture was cooled and poured onto ice/water. The resultant mixture was extracted with ethylacetate then the combined extracts were washed with Seignette salt solution. The organic phase was dried, filtered and evaporated then purified by chromatography (silica, 0 to 60% ethyl acetate in heptane) then trituration with diisopropyl ether to give the title compound (145 mg, 64%) as a white solid. MS: m/e=372.3 [M+H]⁺.

Example 4

6-[(5-Methyl-3-(3,3,3-trifluoro-propyl)-isoxazol-4-yl)methoxy]-N-(tetrahydro-pyran-4-yl)-nicotinamide

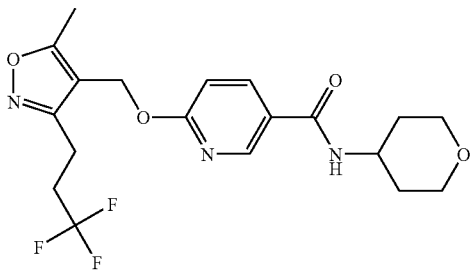 [SMILES: Cc1onc(CCC(F)(F)F)c1COc1ccc(C(=O)NC2CCOCC2)cn1]

As described for example 1e, 6-[5-methyl-3-(3,3,3-trifluoro-propyl)-isoxazol-4-ylmethoxy]-nicotinic acid methyl ester (215 mg, 0.62 mmol) was converted, using 4-aminotetrahydropyran instead of isopropylamine, to the title compound (26 mg, 10%) which was obtained as a white solid after purification by chromatography (silica, 0 to 60% ethyl acetate in heptane) and trituration with ethyl acetate and hexane. MS: m/e=414.3 [M+H]⁺.

Example 5

6-((3-Butyl-5-methyl-isoxazol-4-yl)methoxy)-N-isopropyl-nicotinamide

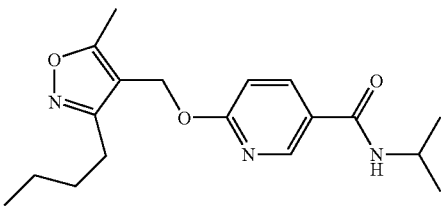 [SMILES: CCCCc1noc(C)c1COc1ccc(C(=O)NC(C)C)cn1]

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl (E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, then the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]⁺.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithium aluminium hydride (2.03 g, 53.4 mmol) in five portions. After 1 h the reaction mixture was quenched dropwise with Seignette salt solution. The reaction mixture was filtered and the filtrate extracted with ethyl acetate. The combined organic extracts were washed with Seignette salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]⁺.

c) 6-(3-Butyl-5-methyl-isoxazol-4-ylmethoxy)-nicotinic acid methyl ester

As described for example 1d, (3-butyl-5-methyl-isoxazol-4-yl)-methanol (1.0 g, 5.9 mmol) was converted, instead of (3-propyl-5-methyl-isoxazol-4-yl)-methanol, to the title compound (905 mg, 45%) which was obtained as a light yellow oil. MS: m/e=305.3 [M+H]⁺.

d) 6-(3-Butyl-5-methyl-isoxazol-4-ylmethoxy)-N-isopropyl-nicotinamide

Trimethylaluminium (3 mL of a 2 M solution in toluene, 6 mmol) was added dropwise to a stirred solution of isopropylamine (355 mg, 6.0 mmol) in dioxane (4 mL) at room temperature and under argon. After 1 h, a solution of 6-(3-butyl-5-methyl-isoxazol-4-ylmethoxy)-nicotinic acid methyl ester (537 mg, 1.5 mmol) in dioxane (4 mL) was added and the reaction mixture warmed to 90° C. After 2 h the reaction mixture was cooled and poured onto ice/water. The resultant mixture was extracted with ethyl acetate then the combined extracts were washed with Seignette salt solution. The organic phase was dried, filtered and evaporated then purified by chromatography (silica, 0 to 60% ethyl acetate in heptane) then trituration with diisopropyl ether to give the title compound (76 mg, 15%) as a white solid. MS: m/e=332.4 [M+H]⁺.

Example 6

6-((3-Butyl-5-methyl-isoxazol-4-yl)methoxy)-N-cyclopropyl-nicotinamide

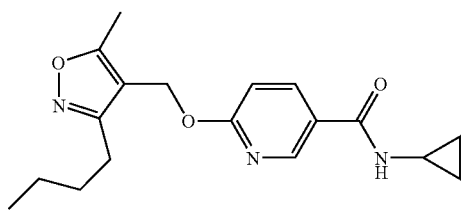 [SMILES: CCCCc1noc(C)c1COc1ccc(C(=O)NC2CC2)cn1]

As described for example 5d, 6-(3-butyl-5-methyl-isoxazol-4-ylmethoxy)-nicotinic acid methyl ester (537 mg, 1.5 mmol) was converted, using cyclopropylamine instead of isopropylamine, to the title compound (85 mg, 17%) which was obtained as a white solid after purification by chromatography (silica, 0 to 50% ethyl acetate in heptane). MS: m/e=330.4 [M+H]+.

Example 7

6-((3-Butyl-5-methyl-isoxazol-4-yl)methoxy)-N-(tetrahydro-pyran-4-yl)-nicotinamide

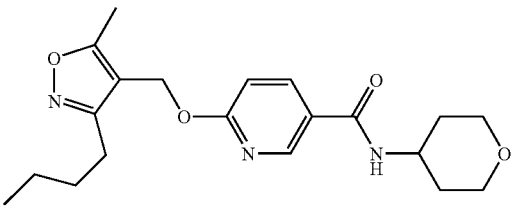

As described for example 5d, 6-(3-butyl-5-methyl-isoxazol-4-ylmethoxy)-nicotinic acid methyl ester (358 mg, 1.2 mmol) was converted, using 4-aminotetrahydropyran instead of isopropylamine, to the title compound (160 mg, 43%) which was obtained as a white solid after purification by chromatography (silica, 0 to 70% ethyl acetate in heptane). MS: m/e=374.3 [M+H]+.

Example 8

6-((3-Butyl-5-methyl-isoxazol-4-yl)methoxy)-N-(2-hydroxy-1,1-dimethyl-ethyl)-nicotinamide

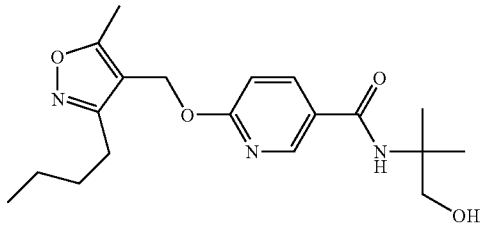 [SMILES: CCCCc1noc(C)c1COc1ccc(C(=O)NC(C)(C)CO)cn1]

As described for example 5d, 6-(3-butyl-5-methyl-isoxazol-4-ylmethoxy)-nicotinic acid methyl ester (537 mg, 1.5 mmol) was converted, using 2-amino-2-methyl-1-propanol instead of isopropylamine, to the title compound (155 mg, 29%) which was obtained as a white solid after purification by chromatography (silica, 0 to 60% ethyl acetate in heptane). MS: m/e=362.4 [M+H]+.

Example 9

Rac-6-((3-Butyl-5-methyl-isoxazol-4-yl)methoxy)-N-(2-hydroxy-1-methyl-ethyl)-nicotinamide

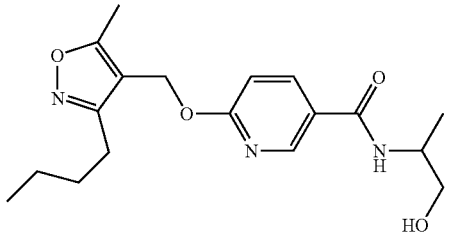 [SMILES: CCCCc1noc(C)c1COc1ccc(C(=O)NC(C)CO)cn1]

A mixture of 6-(3-butyl-5-methyl-isoxazol-4-ylmethoxy)-nicotinic acid methyl ester (250 mg, 0.82 mmol), rac-2-amino-1-propanol (63 mg, 0.84 mmol) and TBD (29 mg, 0.21 mmol) was stirred for 15 h at room temperature under argon. The reaction mixture was concentrated onto silica then purified by chromatography (silica, 0 to 4% methanol in dichloromethane) to give the title compound (145 mg, 60%) as a white solid after trituration with diisopropyl ether. MS: m/e=348.3 [M+H]+.

Example 10

6-((3-Butyl-5-methyl-isoxazol-4-yl)methoxy)-N-(2-hydroxy-ethyl)-nicotinamide

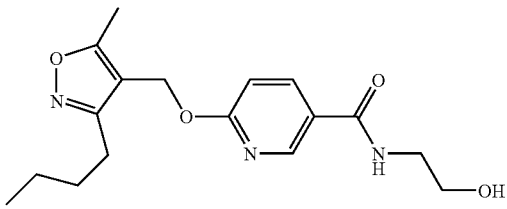 [SMILES: CCCCc1noc(C)c1COc1ccc(C(=O)NCCO)cn1]

As described for example 9, 6-(3-butyl-5-methyl-isoxazol-4-ylmethoxy)-nicotinic acid methyl ester (500 mg, 1.4 mmol) was converted, using ethanolamine instead of rac-2-amino-1-propanol, to the title compound (280 mg, 60%) which was obtained as a colourless oil after purification by chromatography (silica, 0 to 5% methanol in dichloromethane). MS: m/e=334.3 [M+H]+.

Example 11

(+)-6-((3-Butyl-5-methyl-isoxazol-4-yl)methoxy)-N-(2-hydroxy-1-methyl-ethyl)-nicotinamide

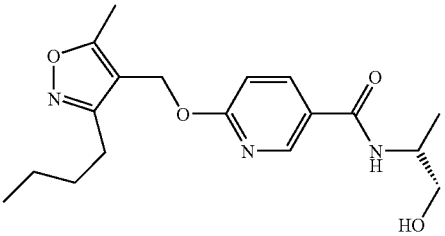

The stereoisomers of rac-6-(3-butyl-5-methyl-isoxazol-4-ylmethoxy)-N-(2-hydroxy-1-methyl-ethyl)-nicotinamide (example 9, 500 mg) in ethanol:heptane (1:1, 4 mL) were separated using a 5×50 cm Chiralpak AD column at room temperature using an isopropanol:heptane (2:8) mobile phase with UV detection at 220 nM. The least polar component (+ve sign of rotation) was obtained as a white solid (200 mg).

Example 12

(−)-6-((3-Butyl-5-methyl-isoxazol-4-yl)methoxy)-N-(2-hydroxy-1-methyl-ethyl)-nicotinamide

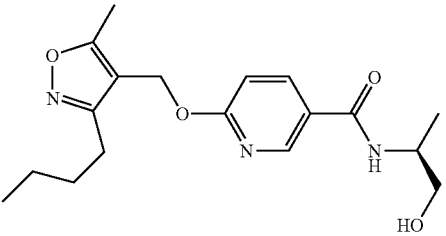 [SMILES: CCCCc1noc(C)c1COc1ccc(C(=O)N[C@@H](C)CO)cn1]

The stereoisomers of rac-6-(3-butyl-5-methyl-isoxazol-4-ylmethoxy)-N-(2-hydroxy-1-methyl-ethyl)-nicotinamide (example 9, 500 mg) in ethanol:heptane (1:1, 4 mL) were separated using a 5×50 cm Chiralpak AD column at room temperature using an isopropanol:heptane (2:8) mobile phase with UV detection at 220 nM. The most polar component (−ve sign of rotation) was obtained as a white solid (170 mg).

Example 13

6-((3-Butyl-5-methyl-isoxazol-4-yl)methoxy)-N-(2-hydroxy-2-methyl-propyl)-nicotinamide

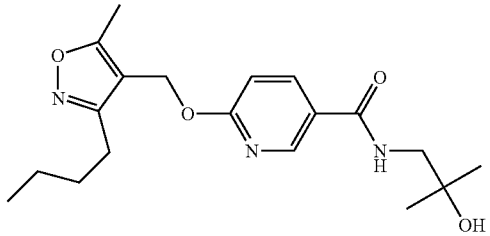 [SMILES: CCCCc1noc(C)c1COc1ccc(C(=O)NCC(C)(C)O)cn1]

As described for example 9, 6-(3-butyl-5-methyl-isoxazol-4-ylmethoxy)-nicotinic acid methyl ester (150 mg, 0.49 mmol) was converted, using 1-amino-2-methyl-propan-2-ol instead of rac-2-amino-1-propanol, to the title compound (10 mg, 6%) which was obtained as a colourless oil after purification by chromatography (silica, 0 to 5% methanol in dichloromethane). MS: m/e=362.3 [M+H]$^+$.

Example 14

6-((3-Butyl-5-methyl-isoxazol-4-yl)methoxy)-N-(tetrahydro-furan-3-yl)-nicotinamide

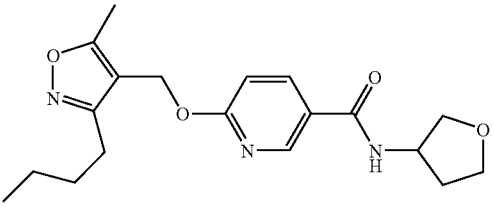

As described for example 5d, 6-(3-butyl-5-methyl-isoxazol-4-ylmethoxy)-nicotinic acid methyl ester (150 mg, 0.49 mmol) was converted, using tetrahydrofuran-3-amine instead of isopropylamine, to the title compound (120 mg, 68%) which was obtained as a white solid after purification by chromatography (silica, 0 to 5% methanol in dichloromethane). MS: m/e=360.4 [M+H]$^+$.

Example 15

6-((3-Butyl-5-methyl-isoxazol-4-yl)methoxy)-N-(2-hydroxy-1-hydroxymethyl-ethyl)-nicotinamide

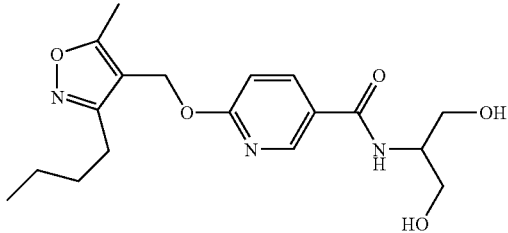 [SMILES: CCCCc1noc(C)c1COc1ccc(C(=O)NC(CO)CO)cn1]

As described for example 9, 6-(3-butyl-5-methyl-isoxazol-4-ylmethoxy)-nicotinic acid methyl ester (150 mg, 0.49 mmol) was converted, using 2-amino-1,3-propanediol instead of rac-2-amino-1-propanol, to the title compound (53 mg, 30%) which was obtained as a white solid after purification by chromatography (silica, 0 to 8% methanol in dichloromethane). MS: m/e=364.3 [M+H]$^+$.

Example 16

6-((3-Butyl-5-methyl-isoxazol-4-yl)methoxy)-N-(S)-tetrahydro-furan-3-yl-nicotinamide

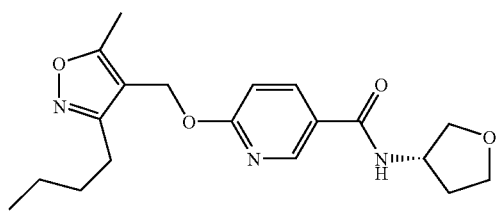 [SMILES: CCCCc1noc(C)c1COc1ccc(C(=O)N[C@H]2CCOC2)cn1]

As described for example 5d, 6-(3-butyl-5-methyl-isoxazol-4-ylmethoxy)-nicotinic acid methyl ester (150 mg, 0.49 mmol) was converted, using (S)-tetrahydrofuran-3-amine hydrochloride instead of isopropylamine, to the title compound (70 mg, 40%) which was obtained as a light yellow oil after purification by chromatography (silica, 0 to 4.5% methanol in dichloromethane). MS: m/e=360.5 [M+H]$^+$.

Example 17

6-((3-Butyl-5-methyl-isoxazol-4-yl)methoxy)-N-(2-hydroxy-propyl)-nicotinamide

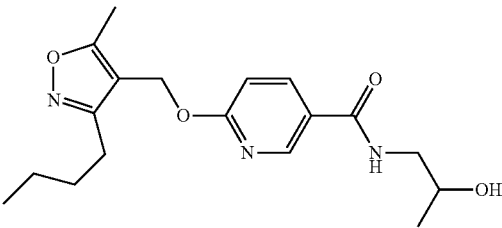 [SMILES: CCCCc1noc(C)c1COc1ccc(C(=O)NCC(C)O)cn1]

As described for example 9, 6-(3-butyl-5-methyl-isoxazol-4-ylmethoxy)-nicotinic acid methyl ester (150 mg, 0.49 mmol) was converted, using rac-1-amino-2-propanol instead of rac-2-amino-1-propanol, to the title compound (5 mg, 3%) which was obtained as a yellow oil after purification by chromatography (silica, 0 to 6% methanol in dichloromethane). MS: m/e=348.3 [M+H]$^+$.

Example 18

[6-((3-Butyl-5-methyl-isoxazol-4-yl)methoxy)-pyridin-3-yl]-(1,1-dioxo-1,6-thiomorpholin-4-yl)-methanone

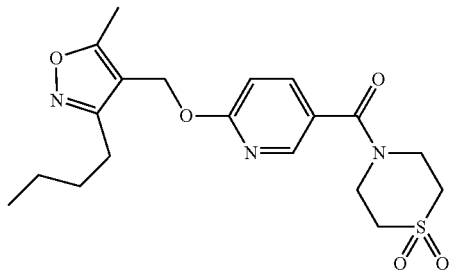 [SMILES: CCCCc1noc(C)c1COc1ccc(C(=O)N2CCS(=O)(=O)CC2)cn1]

As described for example 5d, 6-(3-butyl-5-methyl-isoxazol-4-ylmethoxy)-nicotinic acid methyl ester (150 mg, 0.49 mmol) was converted, using thiomorpholine 1,1-dioxide instead of isopropylamine, to the title compound (21 mg, 9%) which was obtained as a colourless oil after purification by chromatography (silica, 0 to 10% methanol in dichloromethane). MS: m/e=408.3 [M+H]⁺.

Example 19

6-((3-Butyl-5-methyl-isoxazol-4-yl)methoxy)-N—((S)-2,2,2-trifluoro-1-methyl-ethyl)-nicotinamide

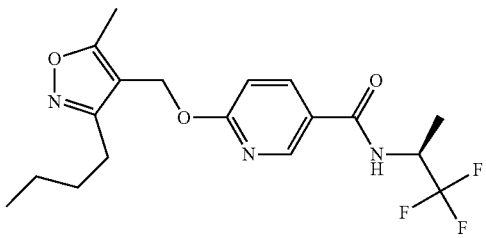 [SMILES: CCCCc1noc(C)c1COc1ccc(C(=O)N[C@@H](C)C(F)(F)F)cn1]

a) 6-(3-Butyl-5-methyl-isoxazol-4-ylmethoxy)-nicotinic acid

To a suspension of 6-(3-butyl-5-methyl-isoxazol-4-ylmethoxy)-nicotinic acid methyl ester (1.0 g, 3.3 mmol) in THF (6 mL) was added a solution of lithium hydroxide monohydrate (248 mg, 9.8 mmol) in water (6 mL) added and the resulting mixture stirred at room temperature for 5 h. The mixture was acidified to pH 4 with HCl (1 N, 4.5 mL) and the resulting mixture extracted with ethyl acetate. The combined organic layers were then washed with water and brine, dried over sodium sulfate and evaporated. Purification by chromatography (silica, heptane:ethyl acetate=1:0 to 0:1) afforded the title compound (654 mg, 76%) which was obtained as a white solid. MS: m/e=291.2 [M+H]⁺.

b) 6-(3-Butyl-5-methyl-isoxazol-4-ylmethoxy)-N-(S)-2,2,2-trifluoro-1-methyl-ethyl)-nicotinamide To a stirred solution of 6-(3-butyl-5-methyl-isoxazol-4-ylmethoxy)-nicotinic acid (100 mg, 0.34 mmol) in DMF (2 mL) at room temperature under argon was added L-2,2,2-trifluoro-1-(methyl)ethylamine (ABCR F07820EFA, 42.9 mg, 0.38 mmol), 2-(1H-benzotriazole-1-yl)-1,1,3,3-tetramethyluronium tetrafluoroborate (121.7 mg, 0.38 mmol) and N,N-diisopropylethylamine (222.6 mg, 1.72 mmol). After 2.5 h the reaction mixture was concentrated, diluted with water and extracted with ethyl acetate. The combined organic extracts were dried over sodium sulfate, filtered and concentrated. Purification by chromatography (silica, heptane:ethyl acetate=1:0 to 2:1) afforded the title compound (89 mg, 67%) as a light yellow oil. MS: m/e=384.3 [M−H]⁻.

Example 20

6-((3-Butyl-5-methyl-isoxazol-4-yl)methoxy)-N—((S)-2,2,2-trifluoro-1-methyl-ethyl)-nicotinamide

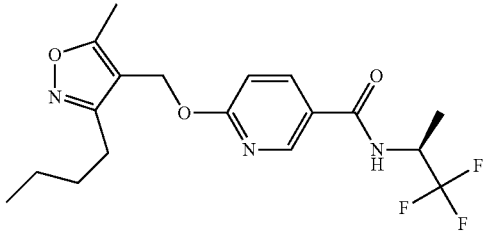 [SMILES: CCCCc1noc(C)c1COc1ccc(C(=O)N[C@@H](C)C(F)(F)F)cn1]

As described for example 19b, 6-(3-butyl-5-methyl-isoxazol-4-ylmethoxy)-nicotinic acid (100 mg, 0.34 mmol) was converted, using L-2,2,2-trifluoro-1-(methyl)ethylamine (ABCR AB146651) instead of L-2,2,2-trifluoro-1-(methyl)ethylamine (ABCR F07820EFA), to the title compound (81 mg, 61%) which was obtained as a light yellow oil after purification by chromatography (silica, heptane:ethyl acetate=1:0 to 2:1). MS: m/e=384.3 [M−H]⁻.

Example 21

6-((3-Butyl-5-methyl-isoxazol-4-yl)methoxy)-N-(1-methyl-cyclopropyl)-nicotinamide

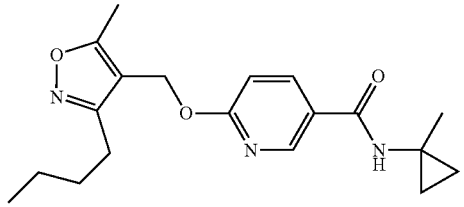 [SMILES: CCCCc1noc(C)c1COc1ccc(C(=O)NC2(C)CC2)cn1]

As described for example 19b, 6-(3-butyl-5-methyl-isoxazol-4-ylmethoxy)-nicotinic acid (100 mg, 0.34 mmol) was converted, using 1-methylcyclopropylamine instead of L-2,2,2-trifluoro-1-(methyl)ethylamine, to the title compound (83 mg, 70%) which was obtained as a white solid after purification by chromatography (silica, heptane:ethyl acetate=1:0 to 2:1). MS: m/e=342.3 [M−H]⁻.

Example 22

Azetidin-1-yl-[6-((3-butyl-5-methyl-isoxazol-4-yl)methoxy)-pyridin-3-yl]-methanone

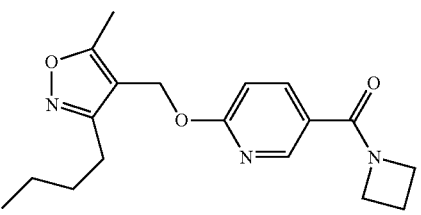 [SMILES: CCCCc1noc(C)c1COc1ccc(C(=O)N2CCC2)cn1]

As described for example 19b, 6-(3-butyl-5-methyl-isoxazol-4-ylmethoxy)-nicotinic acid (100 mg, 0.34 mmol) was converted, using azetidine instead of L-2,2,2-trifluoro-1-(methyl)ethylamine, to the title compound (45 mg, 39%) which was obtained as a light yellow oil after purification by chromatography (silica, heptane:ethyl acetate=1:0 to 2:1). MS: m/e=330.3 [M+H]⁺.

Example 23

6-((3-Butyl-5-methyl-isoxazol-4-yl)methoxy)-N-(1-methyl-1H-pyrazol-4-yl)-nicotinamide

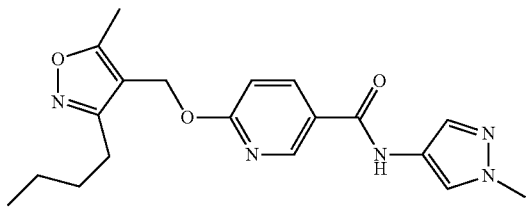 [SMILES: CCCCc1noc(C)c1COc1ccc(C(=O)Nc2cnn(C)c2)cn1]

As described for example 19b, 6-(3-butyl-5-methyl-isoxazol-4-ylmethoxy)-nicotinic acid (100 mg, 0.34 mmol) was converted, using 1-methyl-1H-pyrazol-4-ylamine instead of L-2,2,2-trifluoro-1-(methyl)ethylamine, to the title compound (70 mg, 55%) which was obtained as a yellow oil after purification by chromatography (silica, heptane:ethyl acetate 9:1 to 1:1). MS: m/e=370.2 [M+H]+.

Example 24

6-((3-Butyl-5-methyl-isoxazol-4-yl)methoxy)-N-(1-methyl-1H-pyrazol-3-yl)-nicotinamide

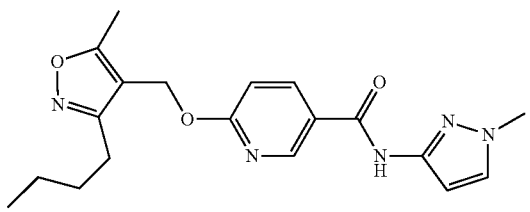 [SMILES: CCCCc1noc(C)c1COc1ccc(C(=O)Nc2ccn(C)n2)cn1]

As described for example 19b, 6-(3-butyl-5-methyl-isoxazol-4-ylmethoxy)-nicotinic acid (100 mg, 0.34 mmol) was converted, using 1-methyl-1H-pyrazol-3-ylamine instead of L-2,2,2-trifluoro-1-(methyl)ethylamine, to the title compound (70 mg, 55%) which was obtained as a yellow oil after purification by chromatography (silica, heptane:ethyl acetate 9:1 to 1:1). MS: m/e=370.2 [M+H]+.

Example 25

6-((3-Butyl-isoxazol-4-yl)methoxy)-N-isopropyl-nicotinamide

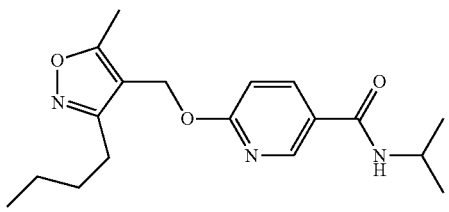 [SMILES: CCCCc1noc(C)c1COc1ccc(C(=O)NC(C)C)cn1]

a) 3-Butyl-isoxazole-4-carboxylic acid ethyl ester

As described for example 1a except using valeraldehyde (12.4 mL, 116 mmol) instead of butyraldehyde, the penatnal oxime intermediate product (11.7 g, 99%) was obtained as a yellow solid and as a mixture of cis and trans isomers that was used directly without further purification. MS (EI): m/e=101.0 [M]+. Then as described for example 1b, except using (E and/or Z)-pentanal oxime (11.4 g, 113 mmol) instead of (E and/or Z)-butanal oxime, and using ethyl 3,3-dimethylaminoacrylate instead of ethyl (E)-3-(1-pyrrolidino)-2-butenoate, the title compound (13.6 g, 61%) was obtained as a yellow liquid after purification by chromatography (silica, 0 to 10% ethyl acetate in heptane). MS: m/e=198.1 [M+H]+.

b) 3-Butyl-isoxazole-4-carboxylic acid

To a suspension of (E and/or Z)-3-butyl-isoxazole-4-carboxylic acid ethyl ester (10.0 g, 51 mmol) in THF (100 mL) was added a solution of lithium hydroxide monohydrate (4.25 g, 101 mmol) in water (100 mL) and then methanol (100 mL) added and the resulting mixture stirred at room temperature for 1 h. The mixture was acidified to pH 1 with HCl (2 N) and the resulting mixture extracted with ethyl acetate. The combined organic layers were then washed with water and brine, dried over sodium sulphate, filtered and evaporated to afford the title compound (8.33 g, 97%) which was obtained as an off white solid. MS: m/e=168.1 [M−H]+.

c) (3-Butyl-isoxazol-4-yl)-methanol

To a solution of 3-butyl-isoxazole-4-carboxylic acid (27.8 g, 164 mmol in THF (495 mL) at −10° C. was added triethylamine (22.9 mL, 164 mmol) and then a solution of ethylchloroformate (15.7 mL, 164 mmol) in THF (85 mL) added keeping the temperature below −5° C. After 1 h the mixture was filtered and the filtrate cooled to −10° C. and a suspension of sodiumborohydride (31.1 g, 821 mmol) in water (165 mL) added over 15 minutes keeping the temperature below 10° C. The mixture was then allowed to warm up to room temperature overnight and diluted with sodium hydroxide (2 N, 82 mL) and extracted with ethyl acetate. The combined organic layers were then washed with water and brine, dried over sodium sulfate and evaporated to afford the title compound (18.6 g, 73%) which was obtained as a colorless liquid after kugelrohr distillation. Bp: 150° C. at 0.4 mbar. MS: m/e=150.1 [M]+.

d) 6-(3-Butyl-isoxazol-4-ylmethoxy)-nicotinic acid methyl ester

As described for example 1d, except using (3-butyl-isoxazol-4-yl)-methanol (8.0 g, 51.6 mmol) instead of (3-propyl-5-methyl-isoxazol-4-yl)-methanol, the title compound (9.6 g, 64%) was obtained as a white solid after purification by chromatography (silica, 0 to 50% ethyl acetate in heptane). MS: m/e=291.0 [M+H]+.

e) 6-(3-Butyl-isoxazol-4-ylmethoxy)-N-isopropyl-nicotinamide

As described for example 5d, 6-(3-butyl-isoxazol-4-ylmethoxy)-nicotinic acid methyl ester (200 mg, 0.69 mmol) was converted, instead of 6-(3-butyl-5-methyl-isoxazol-4-ylmethoxy)-nicotinic acid methyl ester, to the title compound (200 mg, 91%) which was obtained as a light brown solid after purification by chromatography (silica, 40 to 60% ethyl acetate in heptane). MS: m/e=318.3 [M+H]+.

Example 26

6-((3-Butyl-isoxazol-4-yl)methoxy)-N-(2,2,2-trifluoro-ethyl)-nicotinamide

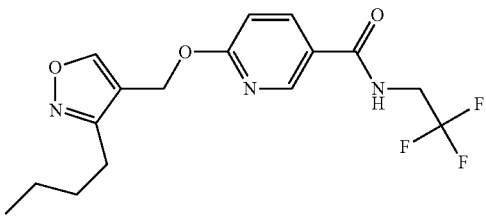 [SMILES: CCCCc1nocc1COc1ccc(C(=O)NCC(F)(F)F)cn1]

As described for example 25e, 6-(3-butyl-isoxazol-4-ylmethoxy)-nicotinic acid methyl ester (200 mg, 0.69 mmol) was converted, using 2,2,2,-trifluoroethylamine instead of isopropylamine, to the title compound (170 mg, 69%) which was obtained as a white solid after purification by chromatography (silica, 30 to 50% ethyl acetate in heptane). MS: m/e=358.1 [M+H]$^+$.

Example 27

6-((3-Butyl-isoxazol-4-yl)methoxy)-N-(tetrahydropyran-4-yl)-nicotinamide

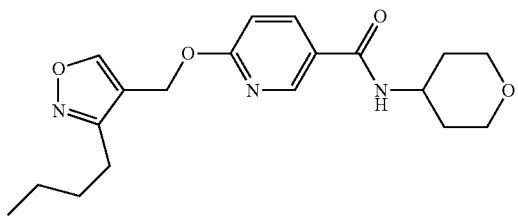 [SMILES: CCCCc1nocc1COc1ccc(C(=O)NC2CCOCC2)cn1]

As described for example 25e, 6-(3-butyl-isoxazol-4-ylmethoxy)-nicotinic acid methyl ester (200 mg, 0.69 mmol) was converted, using 4-aminotetrahydropyran instead of isopropylamine, to the title compound (180 mg, 73%) which was obtained as a white solid after purification by chromatography (silica, 40 to 60% ethyl acetate in heptane). MS: m/e=360.2 [M+H]$^+$.

Example 28

6-((3-Butyl-isoxazol-4-yl)methoxy)-N—((S)-2-hydroxy-1-methyl-ethyl)-nicotinamide

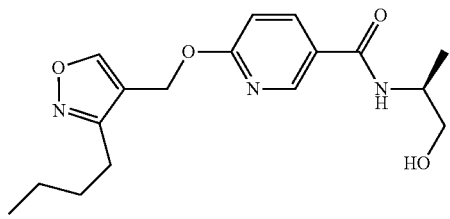 [SMILES: CCCCc1nocc1COc1ccc(C(=O)N[C@@H](C)CO)cn1]

a) 6-(3-Butyl-isoxazol-4-ylmethoxy)-nicotinic acid

To a suspension of 6-(3-butyl-isoxazol-4-ylmethoxy)-nicotinic acid methyl ester (4.0 g, 13.8 mmol) in THF (25 mL) was added a solution of lithium hydroxide monohydrate (1.2 g, 27.6 mmol) in water (25 mL) and then methanol (7 mL) added and the resulting mixture stirred at room temperature for 2 h. The mixture was acidified to pH 1 with HCl (1 N, 80 mL) and the resulting mixture extracted with ethyl acetate. The combined organic layers were then washed with water and brine, dried over sodium sulphate, filtered and evaporated to afford the title compound (3.9 g, 100%) which was obtained as an off white solid. MS: m/e=277.1 [M+H]$^+$.

b) 6-(3-Butyl-isoxazol-4-ylmethoxy)-N—((S)-2-hydroxy-1-methyl-ethyl)-nicotinamide As described for example 19b, 6-(3-butyl-isoxazol-4-ylmethoxy)-nicotinic acid (200 mg, 0.72 mmol) was converted, instead of 6-(3-butyl-5-methyl-isoxazol-4-ylmethoxy)-nicotinic acid, using (S)-(+)-2-amino-1-propanol instead of rac-2,2,2-trifluoro-1-(methyl)ethylamine, to the title compound (190 mg, 79%) which was obtained as a white solid after purification by chromatography (silica, heptane:ethyl acetate 7:3 to 0:1). MS: m/e=332.1 [M–H]$^-$.

Example 29

N-Isopropyl-6-[(5-methyl-3-(1-methyl-butyl)-isoxazol-4-yl)methoxyl]-nicotinamide

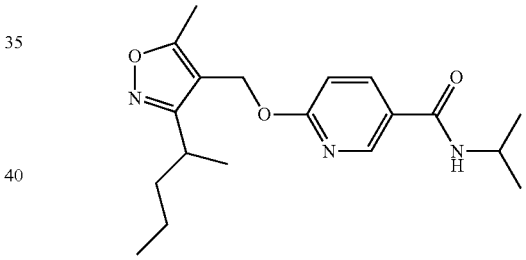

a) [5-Methyl-3-(1-methyl-butyl)-isoxazol-4-yl]-methanol

As described for example 25a except using 2-methyl-N-valeraldehyde (10 g, 100 mmol) instead of valeraldehyde, the oxime intermediate product (12.5 g, 98%) was obtained as a light yellow liquid and as a mixture of cis and trans isomers that was used directly without further purification. MS (EI): m/e=115.0 [M]$^+$. Then as described for example 25b, except using (E and/or Z)-2-methyl-N-valeraldehyde oxime (12.4 g, 100 mmol) instead of (E and/or Z)-pentanal oxime, and using ethyl (E)-3-(1-pyrrolidino)-2-butenoate instead of ethyl 3,3-dimethylaminoacrylate, the isoxazole ester intermediate product (11.3 g, 52%) was obtained as a colourless liquid after purification by chromatography (silica, 0 to 20% ethyl acetate in heptane). To a stirred solution of the ethyl ester (11.2 g, 50 mmol) in THF (120 mL) under argon and at 0° C. was added lithium aluminium hydride (2.17 g, 57 mmol) in five portions. After 90 min the reaction mixture was quenched dropwise with Seignette salt solution. The reaction mixture was filtered and the filtrate extracted with ethyl acetate. The combined organic extracts were washed with Seignette salt solution then dried over sodium sulfate, filtered, concentrated and purified by chromatography (silica, 0 to 60% ethyl acetate in heptane) to give the title compound (7.4 g, 81%) as a colourless oil. MS: m/e=184.1 [M+H]⁺.

b) 6-[5-Methyl-3-(1-methyl-butyl)-isoxazol-4-yl-methoxy]-nicotinic acid methyl ester As described for example 1d, [5-methyl-3-(1-methyl-butyl)-isoxazol-4-yl]-methanol (1.0 g, 5.5 mmol) instead of (3-propyl-5-methyl-isoxazol-4-yl)-methanol, was converted to the title compound (850 mg, 41%) was obtained as a light yellow oil after purification by chromatography (silica, 0 to 10% ethyl acetate in heptane). MS: m/e=319.3 [M+H]

c) N-Isopropyl-6-[5-methyl-3-(1-methyl-butyl)-isoxazol-4-ylmethoxy]-nicotinamide As described for example 9, 6-[5-methyl-3-(1-methyl-butyl)-isoxazol-4-ylmethoxy]-nicotinic acid methyl ester (200 mg, 0.63 mmol), instead of 6-(3-butyl-5-methyl-isoxazol-4-ylmethoxy)-nicotinic acid methyl ester, was converted using isopropylamine instead of rac-2-amino-1-propanol, to the title compound (40 mg, 17%) which was obtained as a colourless oil after purification by chromatography (silica, 0 to 5% methanol in dichloromethane). MS: m/e=346.4 [M+H]

Example 30

6-((3-Cyclopentyl-5-methyl-isoxazol-4-yl)methoxy)-N-isopropyl-nicotinamide

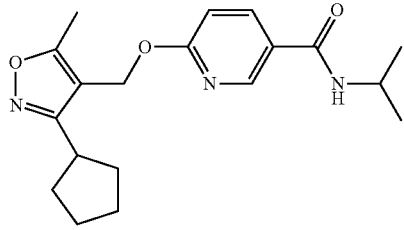

a) (E and/or Z)-Cyclopentanecarbaldehyde oxime

As described for example 29a except using cyclopentylmethanal (10.0 g, 102 mmol) instead of 2-methyl-N-valeraldehyde, the title compound (11.6 g, 100%) was obtained as a yellow liquid and as a mixture of cis and trans isomers that was used directly without further purification.

b) 3-Cyclopentyl-5-methyl-isoxazole-4-carboxylic acid ethyl ester

As described for example 29a, except using cyclopentanecarbaldehyde oxime (11.6 g, 102.5 mmol), the title compound (12.1 g, 53%) was obtained as a yellow liquid after purification by chromatography (silica, 0 to 10% ethyl acetate in heptane). MS: m/e=360.3 [M+H]⁺.

c) (3-Cyclopentyl-5-methyl-isoxazol-4-yl)-methanol

As described for example 29a, except using 3-cyclopentyl-5-methyl-isoxazole-4-carboxylic acid ethyl ester (11.0 g, 49.3 mmol) the title compound (8.1 g, 91%) was obtained as a yellow oil after purification by chromatography (silica, 0 to 60% ethyl acetate in heptane). MS: m/e=182.1 [M+H]⁺.

d) 6-(3-Cyclopentyl-5-methyl-isoxazol-4-yl-methoxy)-nicotinic acid methyl ester

As described for example 29b, except using (3-cyclopentyl-5-methyl-isoxazol-4-yl)-methanol (2.0 g, 11.0 mmol) instead of [5-methyl-3-(1-methyl-butyl)-isoxazol-4-yl]-methanol, the title compound (1.53 g, 41%) was obtained as a colourless oil after purification by chromatography (silica, 0 to 15% ethyl acetate in heptane). MS: m/e=317.1 [M+H]⁺.

e) 6-(3-Cyclopentyl-5-methyl-isoxazol-4-yl-methoxy)-N-isopropyl-nicotinamide

As described for example 5d, 6-(3-cyclopentyl-5-methyl-isoxazol-4-ylmethoxy)-nicotinic acid methyl ester (230 mg, 0.73 mmol) was converted, instead of 6-(3-butyl-5-methyl-isoxazol-4-ylmethoxy)-nicotinic acid methyl ester, to the title compound (155 mg, 62%) which was obtained as a white solid after purification by chromatography (silica, 0 to 80% ethyl acetate in heptane). MS: m/e=344.0 [M+H]⁺.

Example 31

6-((3-Cyclohexyl-5-methyl-isoxazol-4-yl)methoxy)-N-isopropyl-nicotinamide

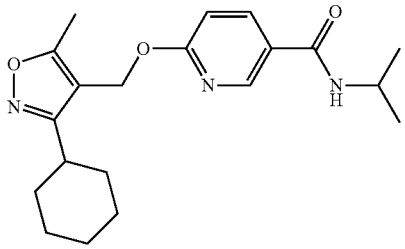 [SMILES: Cc1onc(C2CCCCC2)c1COc1ccc(C(=O)NC(C)C)cn1]

a) (E and/or Z)-Cyclohexanecarbaldehyde oxime

As described for example 30a except using cyclohaxanecarboxyldehyde (10.0 g, 89 mmol) instead of cyclopentylmethanal, the title compound (12.5 g, 99%) was obtained as a light yellow liquid and as a mixture of cis and trans isomers that was used directly without further purification.

b) 3-Cyclohexyl-5-methyl-isoxazole-4-carboxylic acid ethyl ester

As described for example 30b, except using cyclohexanecarbaldehyde oxime (12.4 g, 87.7 mmol) instead of cyclopentanecarbaldehyde oxime, the title compound (9.1 g, 44%) was obtained as a yellow liquid after purification by chromatography (silica, 0 to 10% ethyl acetate in heptane). MS: m/e=238.2 [M+H]⁺.

c) (3-Cyclohexyl-5-methyl-isoxazol-4-yl)-methanol

As described for example 30c, except using 3-cyclohexyl-5-methyl-isoxazole-4-carboxylic acid ethyl ester (8.00 g, 33.7 mmol) instead of 3-cyclopentyl-5-methyl-isoxazole-4-carboxylic acid ethyl ester, the title compound (5.96 g, 91%) was obtained as a yellow oil after purification by chromatography (silica, 0 to 60% ethyl acetate in heptane). MS: m/e=196.1 [M+H]⁺.

d) 6-(3-Cyclohexyl-5-methyl-isoxazol-4-yl-methoxy)-nicotinic acid methyl ester As described for example 30d, except using (3-cyclohexyl-5-methyl-isoxazol-4-yl)-methanol (5.3 g, 27.1 mmol) instead of (3-cyclopentyl-5-methyl-isoxazol-4-yl)-methanol, the title compound (4.17 g, 33%) was obtained as a light yellow oil after purification by chromatography (silica, 0 to 15% ethyl acetate in heptane). MS: m/e=331.4 [M+H]$^+$.

e) N-Isopropyl-6-[5-methyl-3-cyclohexyl-isoxazol-4-ylmethoxy]-nicotinamide

As described for example 30d, 6-(3-cyclohexyl-5-methyl-isoxazol-4-ylmethoxy)-nicotinic acid methyl ester (708 mg, 1.5 mmol), instead of 6-(3-cyclopentyl-5-methyl-isoxazol-4-ylmethoxy)-nicotinic acid methyl ester, was converted to the title compound (19 mg, 4%) which was obtained as a white solid after purification by chromatography (silica, 0 to 5% methanol in dichloromethane) and trituration with diisopropyl ether. MS: m/e=358.5 [M+H]$^+$.

Example 32

6-((3-Cyclohexyl-5-methyl-isoxazol-4-yl)methoxy)-N-cyclopropyl-nicotinamide

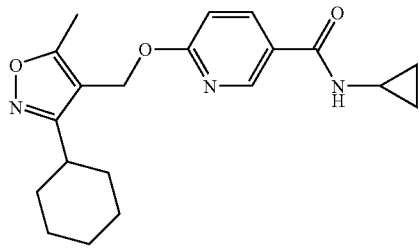 [SMILES: Cc1onc(C2CCCCC2)c1COc1ccc(C(=O)NC2CC2)cn1]

As described for example 31e, 6-(3-cyclohexyl-5-methyl-isoxazol-4-ylmethoxy)-nicotinic acid methyl ester (708 mg, 1.5 mmol) was converted, using cyclopropylamine instead of isopropylamine, to the title compound (219 mg, 41%) which was obtained as a white solid after purification by chromatography (silica, 0 to 60% ethyl acetate in heptane). MS: m/e=356.3 [M+H]$^+$.

Example 33

6-((3-Cyclohexyl-5-methyl-isoxazol-4-yl)methoxy)-N-(tetrahydro-pyran-4-yl)-nicotinamide

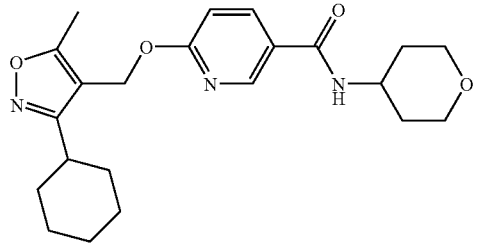 [SMILES: Cc1onc(C2CCCCC2)c1COc1ccc(C(=O)NC2CCOCC2)cn1]

As described for example 31e, 6-(3-cyclohexyl-5-methyl-isoxazol-4-ylmethoxy)-nicotinic acid methyl ester (472 mg, 1.0 mmol) was converted, using 4-aminotetrahydropyran instead of isopropylamine, to the title compound (155 mg, 39%) which was obtained as a white solid after purification by chromatography (silica, 0 to 70% ethyl acetate in heptane). MS: m/e=400.3 [M+H]$^+$.

Example 34

6-((3-Cyclohexyl-5-methyl-isoxazol-4-yl)methoxy)-N-(2-hydroxy-ethyl)-nicotinamide

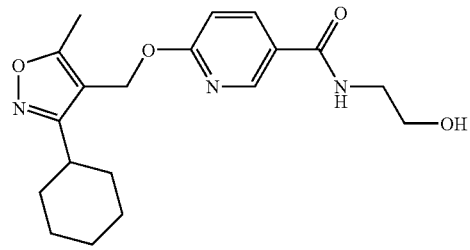 [SMILES: Cc1onc(C2CCCCC2)c1COc1ccc(C(=O)NCCO)cn1]

As described for example 31e, 6-(3-cyclohexyl-5-methyl-isoxazol-4-ylmethoxy)-nicotinic acid methyl ester (708 mg, 1.5 mmol) was converted, using ethanolamine instead of isopropylamine, to the title compound (55 mg, 10%) which was obtained as a light yellow oil after purification by chromatography (silica, 0 to 5% methanol in dichloromethane). MS: m/e=360.4 [M+H]$^+$.

Example 35

6-((3-Cyclohexyl-5-methyl-isoxazol-4-yl)methoxy)-N-(2-hydroxy-1,1-dimethyl-ethyl)-nicotinamide

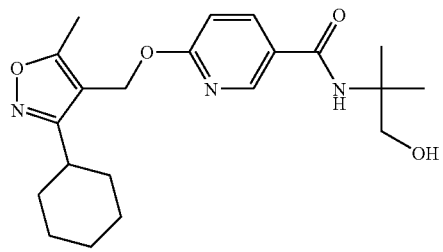 [SMILES: Cc1onc(C2CCCCC2)c1COc1ccc(C(=O)NC(C)(C)CO)cn1]

As described for example 31e, 6-(3-cyclohexyl-5-methyl-isoxazol-4-ylmethoxy)-nicotinic acid methyl ester (708 mg, 1.5 mmol) was converted, using 2-amino-2-methyl-1-propanol instead of isopropylamine, to the title compound (340 mg, 58%) which was obtained as a white solid after purification by chromatography (silica, 0 to 4% methanol in dichloromethane). MS: m/e=388.4 [M+H]$^+$.

Example 36

6-((3-Cyclohexyl-5-methyl-isoxazol-4-yl)methoxy)-N-(2-hydroxy-1-methyl-ethyl)-nicotinamide

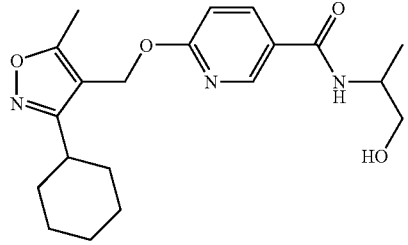 [SMILES: Cc1onc(C2CCCCC2)c1COc1ccc(C(=O)NC(C)CO)cn1]

A mixture of 6-(3-cyclohexyl-5-methyl-isoxazol-4-yl-methoxy)-nicotinic acid methyl ester (500 mg, 1.1 mmol), rac-2-amino-1-propanol (95 mg, 1.3 mmol) and TBD (44 mg, 0.31 mmol) was heated at 50° C. for 15 h under argon. The reaction mixture was concentrated onto silica then purified by chromatography (silica, 0 to 5% methanol in dichloromethane) to give the title compound (290 mg, 73%) as a white solid. MS: m/e=374.4 [M+H]+.

Example 37

N-Isopropyl-6-[(5-methyl-3-(tetrahydro-pyran-4-yl)-isoxazol-4-yl)methoxy]-nicotinamide

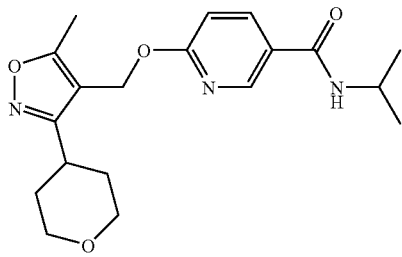 [SMILES: Cc1onc(C2CCOCC2)c1COc1ccc(C(=O)NC(C)C)cn1]

a) Tetrahydro-pyran-4-carbaldehyde oxime

To a suspension of tetrahydro-pyran-4-carbaldehyde (36.9 g, 259 mmol) and hydroxylamine (27.2 g, 388 mmol) in ethanol (246 mL) and water (246 mL) was added sodium acetate) 42.9 g, 517 mmol) and the resulting mixture heated at 90° C. overnight. After cooling to room temperature the resulting mixture was then evaporated and extracted with diethylether and water. The organic extract was then washed with water, brine, dried over sodium sulfate and evaporated. Purification by chromatography (silica, heptane:ethyl acetate=1:1) afforded the title compound (16.8 g, 50%) which was obtained as a yellow liquid. MS: m/e=129.1 [M+H]+.

b) 5-Methyl-3-(tetrahydro-pyran-4-yl)-isoxazole-4-carboxylic acid ethyl ester

To a solution of tetrahydro-pyran-4-carbaldehyde oxime (6.5 g, 50 mmol) in DMF (47 mL) was added N-chlorosuccinimide (6.95 g, 50 mmol) at room temperature and the after 3 h the mixture was extracted with tert-butylmethylether (100 mL). The organic extract was then added dropwise over 2 h to a solution of ethyl 2-butynoate (61.2 mL, 52.5 mmol) and triethylamine (8.4 mL, 60 mmol) in tert-butylmethylether (47 mL) heated under reflux and the resulting mixture heated overnight. The reaction mixture was then cooled to room temperature and extracted with tert-butylmethylether and washed with aqueous hydrochloric acid solution (1 N). The combined organic phases were dried over sodium sulfate, filtered and concentrated. Purification by chromatography (silica, heptane:ethyl acetate=100:0 to 1:1) afforded the title compound (4.2 g, 35%) as a light yellow solid. MS: m/e=240.2 [M+H]+.

c) [5-Methyl-3-(tetrahydro-pyran-4-yl)-isoxazol-4-yl]-methanol

To a solution of 5-methyl-3-(tetrahydro-pyran-4-yl)-isoxazole-4-carboxylic acid ethyl ester (4.0 g, 16.7 mmol) in THF (55 mL) at 0° C. was added lithium aluminum hydride (349 mg, 9.0 mmol). And the resulting mixture stirred for 18 h at room temperature. Water (0.5 mL) was added carefully followed by aqueous sodium hydroxide (15%, 1.0 mL) and water (2.2 mL). The resulting suspension was stirred for 15 min at ambient temperature and filtered over Hyflo®. The filtrate was then evaporated and purification by chromatography (silica, heptane:ethyl acetate=100:0 to 1:1) afforded the title compound (1.1 g, 34%) as a colourless gum. MS: m/e=198.1 [M+H]+.

d) 6-[5-Methyl-3-(tetrahydro-pyran-4-yl)-isoxazol-4-ylmethoxy]-nicotinic acid methyl ester To a stirred solution of 6-hydroxy-nicotinic acid methyl ester (1.67 g, 10.9 mmol) and [5-methyl-3-(tetrahydro-pyran-4-yl)-isoxazol-4-yl]-methanol (2.15 g, 10.9 mmol) in THF (55 mL) at 5° C. under argon was added triphenylphosphine (10.6 g, 39 mmol), then diisopropyl azodicarboxylate (40%, 6.5 mL, 14.2 mmol) was added dropwise. The reaction mixture was warmed to room temperature for 2 h. The reaction mixture was then extracted with tert-butyl methyl ether, and washed with aqueous HCl (2 N) and the organic extract washed with water, dried over sodium sulphate, filtered and evaporated. Purification by chromatography (silica, heptane:ethyl acetate=1:0 to 1:1) afforded the title compound (1.31 g, 36%) as a white solid. MS: m/e=333.2 [M+H]+.

e) N-Isopropyl-6-[5-methyl-3-(tetrahydro-pyran-4-yl)-isoxazol-4-ylmethoxy]-nicotinamide As described for example 31e, 6-[5-methyl-3-(tetrahydro-pyran-4-yl)-isoxazol-4-ylmethoxy]-nicotinic acid methyl ester (100 mg, 0.3 mol), instead of 6-(3-cyclohexyl-5-methyl-isoxazol-4-ylmethoxy)-nicotinic acid methyl ester was converted, to the title compound (80 mg, 74%) which was obtained as a white solid after purification by chromatography (silica, 30 to 70% ethyl acetate in heptane). MS: m/e=360.3 [M+H]+.

Example 38

N—((S)-2-Hydroxy-1-methyl-ethyl)-6-[(5-methyl-3-(tetrahydro-pyran-4-yl)-isoxazol-4-yl)methoxy]-nicotinamide

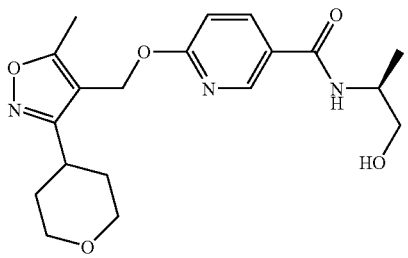 [SMILES: Cc1onc(C2CCOCC2)c1COc1ccc(C(=O)N[C@@H](C)CO)cn1]

A mixture of 6-[5-methyl-3-(tetrahydro-pyran-4-yl)-isoxazol-4-ylmethoxy]-nicotinic acid methyl ester (100 mg, 0.3 mol), S-(+)-2-amino-1-propanol (28.8 μL, 0.36 mmol) and TBD (12.8 mg, 0.09 mmol) was heated at 50° C. for 18 h under argon. The reaction mixture was concentrated onto silica then purified by chromatography (silica, 0 to 15% methanol in ethyl acetate) to give the title compound (30 mg, 27%) as a white solid. MS: m/e=374.4 [M+H]⁺.

Example 39

6-((3-Isobutoxy-5-methyl-isoxazol-4-yl)methoxy)-N-isopropyl-nicotinamide

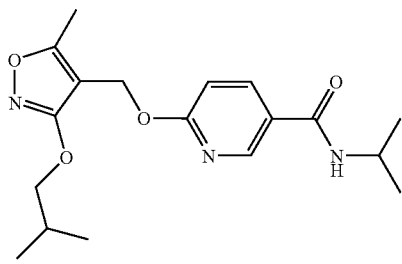 [SMILES: Cc1onc(OCC(C)C)c1COc1ccc(C(=O)NC(C)C)cn1]

a) 3-Isobutoxy-5-methyl-isoxazole

To a stirred solution of 3-hydroxy-5-methylisoxazole (5.0 g, 50.5 mmol) in acetone (125 mL) at room temperature under argon was added K₂CO₃ (13.9 g, 101 mmol) and the reaction mixture was heated at 60° C. After 30 min, 1-bromo-2-methylpropane (10.4 g, 75.7 mmol) was added dropwise over 2 min. After 16 h the reaction mixture was cooled, filtered and concentrated. Purification by chromatography (silica, 70 to 100% ethyl acetate in heptane) gave the title compound (700 mg, 9%) as a volatile yellow liquid.

b) 4-Iodo-3-isobutoxy-5-methyl-isoxazole

To a stirred solution of 3-isobutoxy-5-methyl-isoxazole (570 mg, 3.67 mmol) in AcOH (15 mL) and water (18 mL) at ambient temperature was added ICl (716 mg, 4.40 mmol) and the reaction mixture heated at 80° C. After 2 h the reaction mixture was cooled to room temperature. After 14 h, a solution of sodium sulfite (Na₂SO₃, 1 g) in water (15 mL) was added and the reaction mixture extracted into ethyl acetate (2×50 mL). The combined extracts were washed with water (3×30 ml) and brine then dried over sodium sulfate, filtered and concentrated. Purification by chromatography (silica, 0-10% ethyl acetate in heptane) gave the title compound (706 mg, 68%) as a colourless liquid.

c) 3-Isobutoxy-5-methyl-isoxazole-4-carboxylic acid

To a stirred solution of 4-iodo-3-isobutoxy-5-methyl-isoxazole (669 mg, 2.38) in THF (10 mL) at −30° C. and under argon was added isopropylmagnesium bromide (1.49 mL of a 2.0 M solution in THF) dropwise. The reaction mixture was warmed to 0° C. and stirred for 1 h, then 1,3,5-trioxane (429 mg, 4.76 mmol) in THF (1 mL) was added and the reaction mixture warmed to 50° C. After 1.5 h to the reaction mixture was added further 1,3,5-trioxane (860 mg, 9.52 mmol) and the reaction mixture heated at 70° C. After 2 h the mixture was cooled to 0° C. and solid CO₂ (~10 g) added. After 1 h the reaction mixture was diluted with water (15 mL) then extracted with diethylether. The aqueous phase was acidified with HCl (1 N, 10 mL), then the resultant precipitate filtered off and washed with water (5 mL), then dried under vacuum (60° C.) to afford the title compound (152 mg, 32%) as a white solid. MS: m/e=198.4 [M−H]⁻.

d) (3-Isobutoxy-5-methyl-isoxazol-4-yl)-methanol

To a stirred solution of 3-isobutoxy-5-methyl-isoxazole-4-carboxylic acid (146 mg, 0.73 mmol) and triethylamine (74 mg, 0.73 mmol) in tetrahydrofuran (5 mL) at −10° C. and under argon was added ethyl chloroformate (80 mg, 1.46 mmol). After 30 min, the mixture was filtered and the filter cake washed with tetrahydrofuran (4 mL). The combined filtrates were added to a solution of sodium borohydride (69 mg, 1.83 mmol) in water (2 mL) at 5° C. After 2 h the mixture was concentrated in vacuo, diluted with NaOH (2 N, 4 mL) then dried, filtered and concentrated in vacuo to give the title compound (111 mg, 82%) as a pale yellow oil. MS: m/e=186.3 [M+H]⁺.

e) 6-(3-Isobutoxy-5-methyl-isoxazol-4-ylmethoxy)-nicotinic acid methyl ester

As described for example 37d, (3-isobutoxy-5-methyl-isoxazol-4-yl)-methanol (90 mg, 0.49 mmol) instead of [5-methyl-3-(tetrahydro-pyran-4-yl)-isoxazol-4-yl]-methanol, was converted to the title compound (64 mg, 33%) which was obtained as a colourless gum after purification by chromatography (silica, 0 to 20% ethyl acetate in heptane). MS: m/e=321.3 [M+H]⁺.

f) 6-(3-Isobutoxy-5-methyl-isoxazol-4-ylmethoxy)-N-isopropyl-nicotinamide

As described for example 37e, 6-(3-isobutoxy-5-methyl-isoxazol-4-ylmethoxy)-nicotinic acid methyl ester (62 mg, 0.19 mmol) instead of 6-[5-methyl-3-(tetrahydro-pyran-4-yl)-isoxazol-4-ylmethoxy]-nicotinic acid methyl ester, the title compound (32 mg, 4%) which was obtained as a white solid after purification by chromatography (silica, 10 to 70% ethyl acetate in heptane). MS: m/e=348.5 [M+H]⁺.

Example 40

N-Isopropyl-6-((5-methyl-3-pyrrolidin-1-yl-isoxazol-4-yl)methoxy)-nicotinamide

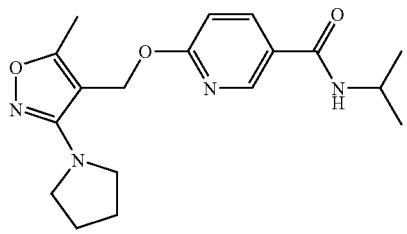

a) Hydroxycarbonimidic dibromide

A solution of glyoxylic acid (37.0 g, 500 mmol) and hydroxylamine hydrochloride (35.1 g, 500 mmol) in water (125 mL) was stirred for 1 h and then sodium hydroxide (50.93 g, 1.27 mmol) added with ice batch cooling. Then a solution of sodium phosphate monobasic H₂O (138 g, 1 mol) was added. The reaction mixture was then cooled to 10-15° C. bromine (51.22 mL, 1 mol) was added over 2 h. The resulting reaction mixture was stirred over night at room temperature, then the reaction mixture was dilated with water and extracted with dichloromethane, and the resulting organic phase was dried over sodium sulfate, filtered and evaporated to afford the title compound (22.0 g, 22%) as an orange solid which was used directly in the next step.

b) 3-Bromo-5-methyl-isoxazole-4-carboxylic acid ethyl ester

To a solution of ethyl 2-pentynoate (16.09 mL, 138 mmol) in dichloromethane (80 mL) was added potassium carbonate (20.65 g, 147.9 mmol) and then a solution of hydroxycarbonimidic dibromide (20.0 g, 98.6 mmol) in dichloromethane (100 mL) was added. The reaction mixture was stirred at room temperature over night. The solvent was then removed and purification by filtration (silica, dichloromethane then ethyl acetate) afforded the title compound (26.3 g, 88%) as a light yellow oil. MS: m/e=234.0 [M]$^+$.

c) 5-Methyl-3-pyrrolidin-1-yl-isoxazole-4-carboxylic acid ethyl ester

A mixture containing 3-bromo-5-methyl-isoxazole-4-carboxylic acid ethyl ester (5.0 g, 18.8 mmol), pyrrolidine (13.37 g, 188 mmol) and BEMP (10.53 g, 37.6 mmol) was heated in the microwave at 180° C. for 10 min. The mixture was then extracted with ethyl acetate, dried over potassium sulphate, filtered and evaporated. Purification by chromatography (silica, ethyl acetate:methanol 1:9 to 3:7) afforded the title compound (1.1 g, 21%) as a yellow oil. MS: m/e=225.3 [M]$^+$.

d) (5-Methyl-3-pyrrolidin-1-yl-isoxazol-4-yl)-methanol

As described for example 1c, 5-methyl-3-pyrrolidin-1-yl-isoxazole-4-carboxylic acid ethyl ester (1.1 g, 3.9 mmol) instead of 3-propyl-5-methyl-isoxazole-4-carboxylic acid ethyl ester, was converted to the title compound (790 mg, 90%) which was obtained as a yellow oil after purification by chromatography (silica, 20 to 50% ethyl acetate in heptane). MS: m/e=183.2 [M+H]$^+$.

e) 6-(5-Methyl-3-pyrrolidin-1-yl-isoxazol-4-ylmethoxy)-nicotinic acid methyl ester As described for example 1d, (5-methyl-3-pyrrolidin-1-yl-isoxazol-4-yl)-methanol (790 mg, 3.9 mmol) instead of (3-propyl-5-methyl-isoxazol-4-yl)-methanol, was converted to the title compound (350 mg, 28%) which was obtained as a colourless oil after purification by chromatography (silica, 20 to 50% ethyl acetate in heptane). MS: m/e=318.2 [M+H]$^+$.

f) N-Isopropyl-6-(5-methyl-3-pyrrolidin-1-yl-isoxazol-4-ylmethoxy)-nicotinamide

As described for example 1e, 6-(5-methyl-3-pyrrolidin-1-yl-isoxazol-4-ylmethoxy)-nicotinic acid methyl ester (100 mg, 0.28 mmol), instead of 6-[5-methyl-3-(3,3,3-trifluoropropyl)-isoxazol-4-ylmethoxy]-nicotinic acid methyl ester, was converted, to the title compound (30 mg, 55%) which was obtained as a white solid after purification by chromatography (silica, 30 to 60% ethyl acetate in heptane). MS: m/e=345.2 [M+H]$^+$.

Example 41

6-((5-methyl-3-pyrrolidin-1-yl-isoxazol-4-yl)methoxy)-N-(tetrahydro-pyran-4-yl)-nicotinamide

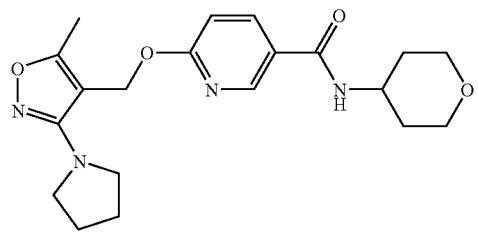 [SMILES: Cc1onc(N2CCCC2)c1COc1ccc(C(=O)NC2CCOCC2)cn1]

As described for example 40f, 6-(5-methyl-3-pyrrolidin-1-yl-isoxazol-4-ylmethoxy)-nicotinic acid methyl ester (100 mg, 0.28 mmol), was converted, using 4-aminotetrahydropyran instead of isopropylamine, to the title compound (30 mg, 49%) which was obtained as a white solid after purification by chromatography (silica, 40 to 90% ethyl acetate in heptane). MS: m/e=387.2 [M+H]$^+$.

Example 42

6-[((3-Butyl-5-methyl-isoxazol-4-yl)methyl)-amino]-N-isopropyl-nicotinamide

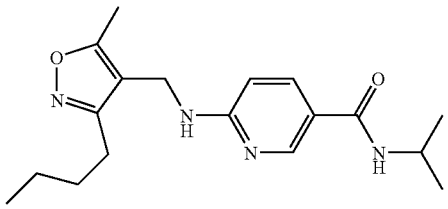 [SMILES: CCCCc1noc(C)c1CNc1ccc(C(=O)NC(C)C)cn1]

a) 3-Butyl-4-chloromethyl-5-methyl-isoxazole

To a solution of (3-butyl-5-methyl-isoxazol-4-yl)-methanol (1.00 g, 5.9 mmol) in dichloromethane (10 mL) was added thionyl chloride (1.41 g, 11.8 mmol) dropwise at 0° C. After 1 h, the reaction mixture was evaporated to afford the title compound (980 mg, 88%) as a light brown liquid. MS: m/e=208.1 [M+H]$^+$.

b) 2-(3-Butyl-5-methyl-isoxazol-4-ylmethyl)-isoindole-1,3-dione

Phthalimide potassium was suspended in DMF (35 mL) and the reaction mixture heated to 90° C. A solution of 3-butyl-4-chloromethyl-5-methyl-isoxazole (970 mg, 5.2 mmol) in DMF (25 mL) was added. After 45 min the reaction mixture was cooled, evaporated and the residue obtained was diluted with water then extracted with ether. The combined organic extracts were dried, filtered and concentrated then purified by chromatography (silica, 0 to 50% ethyl acetate in heptane) to give the title compound (1.21 g, 78%) as an off white solid that was used directly in the next step.

c) C-(3-Butyl-5-methyl-isoxazol-4-yl)-methylamine 2-(3-Butyl-5-methyl-isoxazol-4-ylmethyl)-isoindole-1,3-dione (1.20 g, 4.0 mmol) was dissolved in MeOH (20 mL) then hydrazine hydrate (1.51 g, 30.1 mmol) was added and the reaction mixture heated at 55° C. After 2 h the reaction mixture was cooled and filtered. The filtrate was evaporated and purified by chromatography (silica, 2 to 10% methanol in dichloromethane) to give the title compound (550 mg, 81%) as a yellow liquid. MS: m/e=348.5 [M+H]$^+$.

d) 6-[(3-Butyl-5-methyl-isoxazol-4-ylmethyl)-amino]-nicotinic acid methyl ester C-(3-Butyl-5-methyl-isoxazol-4-yl)-methylamine (320 mg, 1.90 mmol) was dissolved in DMSO (3 mL), methyl 6-chloronicotinate (326 mg, 1.90 mmol) and N,N-diisopropylethylamine (492 mg, 3.80 mmol) added, and the reaction mixture heated under microwave irradiation at 160° C. for 1 h. The reaction mixture was poured onto ice-water and extracted with ethyl acetate. The combined organic extracts were dried, filtered and concentrated then purified by chromatography (silica, 0 to 50% ethyl acetate in heptane) to give the title compound (280 mg, 49%) as a white solid. MS: m/e=348.5 [M+H]$^+$.

e) 6-[(3-Butyl-5-methyl-isoxazol-4-ylmethyl)-amino]-N-isopropyl-nicotinamide As described for example 5d, 6-[(3-butyl-5-methyl-isoxazol-4-ylmethyl)-amino]-nicotinic acid methyl ester (90 mg, 0.3 mmol) was converted, instead of 6-(3-butyl-5-methyl-isoxazol-4-ylmethoxy)-nicotinic acid methyl ester, to the title compound (69 mg, 70%) which was obtained as a white foam after purification by chromatography (silica, 0 to 7% methanol in dichloromethane). MS: m/e=331.4 [M+H]$^+$.

Example 43

6-[((3-Butyl-5-methyl-isoxazol-4-yl)methyl)-amino]-N-(2-hydroxy-1-methyl-ethyl)-nicotinamide

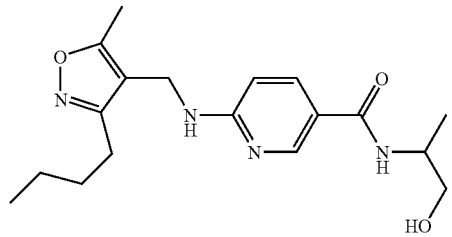 [SMILES: CCCCc1noc(C)c1CNc1ccc(C(=O)NC(C)CO)cn1]

A mixture of 6-[(3-butyl-5-methyl-isoxazol-4-ylmethyl)-amino]-nicotinic acid methyl ester (90 mg, 0.3 mmol), rac-2-amino-1-propanol (27 mg, 0.36 mmol) and TBD (12 mg, 0.09 mmol) was heated at 50° C. for 4 h under argon. The reaction mixture was concentrated onto silica then purified by chromatography (silica, 0 to 7% methanol in ethyl acetate) to give the title compound (55 mg, 54%) as a colourless oil. MS: m/e=347.3 [M+H]$^+$.

Example 44

6-[((3-Butyl-5-methyl-isoxazol-4-yl)methyl)-amino]-N-(tetrahydro-pyran-4-yl)-nicotinamide

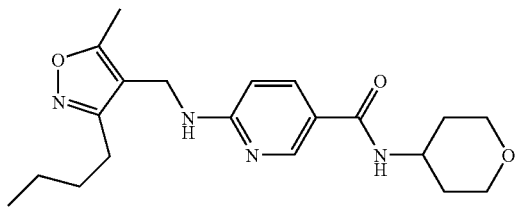 [SMILES: CCCCc1noc(C)c1CNc1ccc(C(=O)NC2CCOCC2)cn1]

a) 6-[(3-Butyl-5-methyl-isoxazol-4-ylmethyl)-amino]-nicotinic acid

To a suspension of 6-[(3-butyl-5-methyl-isoxazol-4-ylmethyl)-amino]-nicotinic acid methyl ester (1.09 g, 4.0 mmol) in THF (11 mL) was added a solution of lithium hydroxide monohydrate (302 mg, 7.0 mmol) in water (11 mL) and methanol (11 mL). The resulting mixture was stirred at room temperature overnight. The mixture was acidified to pH 4 with HCl (1 N) and the resulting mixture diluted with diethylether. The aqueous phase was removed and the organic phase triturated with hexane-diethylether to afford the title compound (910 mg, 87%) which was obtained as a white solid. MS: m/e=288.4 [M−H]$^-$.

b) 6-[(3-Butyl-5-methyl-isoxazol-4-ylmethyl)-amino]-N-(tetrahydro-pyran-4-yl)-nicotinamide As described for example 19b, 6-[(3-butyl-5-methyl-isoxazol-4-ylmethyl)-amino]-nicotinic acid (70 mg, 0.24 mmol) instead of 6-(3-butyl-5-methyl-isoxazol-4-ylmethoxy)-nicotinic acid, was converted, using 4-aminotetrahydropyran instead of rac-2,2,2-trifluoro-1-(methyl)ethylamine, to the title compound (77 mg, 86%) which was obtained as an off white foam after purification by chromatography (silica, heptane:ethyl acetate=1:0 to 2:1). MS: m/e=373.3 [M+H]$^+$.

The invention claimed is:
1. A compound of formula I

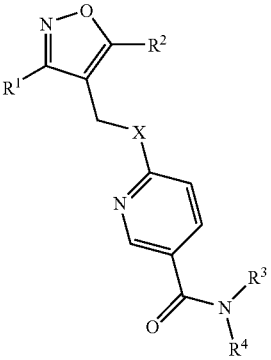

wherein
X is O or NH;
R$^1$ is
  a) lower-alkyl or lower-alkoxy, each optionally substituted with 1, 2, 3 or 4 substituents independently selected from the group consisting of halogen, cyano, hydroxy and lower-alkoxy, or
  b) cycloalkyl or heterocyclyl, each optionally substituted with 1, 2, 3 or 4 substituents independently selected from the group consisting of halogen, cyano, hydroxy, lower-alkyl and lower-alkoxy;
R$^2$ is hydrogen or lower-alkyl optionally substituted with 1, 2, 3 or 4 substituents independently selected from the group consisting of halogen, cyano and lower-alkoxy;
R$^3$ is hydrogen or lower-alkyl optionally substituted with 1, 2, 3 or 4 substituents independently selected from the group consisting of halogen, cyano, hydroxy and lower-alkoxy;
R$^4$ is lower-alkyl, cycloalkyl, heterocyclyl or heteroaryl, each optionally substituted with 1, 2, 3 or 4 substituents independently selected from the group consisting of halogen, cyano, hydroxy, oxo, lower alkyl and lower-alkoxy;
or wherein R$^3$ and R$^4$, together with the nitrogen atom to which they are attached, form a heterocyclyl, optionally substituted with 1, 2, 3 or 4 substituents independently selected from the group consisting of halogen, cyano, hydroxy, lower-alkyl, lower-alkoxy and oxo;

or a pharmaceutically acceptable salt and ester thereof.

2. The compound of claim 1, wherein X is O.

3. The compound of claim 1, wherein $R^1$ is lower-alkyl, lower-alkyl substituted by halogen, cycloalkyl, lower-alkoxy or heterocyclyl.

4. The compound of claim 3, wherein $R^1$ is lower-alkyl, cycloalkyl, lower-alkoxy or pyrrolidinyl.

5. The compound of claim 4, wherein $R^1$ is butyl, cyclohexyl, isobutoxy or pyrrolidin-1-yl.

6. The compound of claim 1, wherein $R^2$ is hydrogen or lower-alkyl.

7. The compound of claim 6, wherein $R^2$ is lower-alkyl.

8. The compound of claim 7, wherein $R^2$ is methyl.

9. The compound of claim 1, wherein $R^3$ is hydrogen.

10. The compound of claim 1, wherein $R^4$ is lower-alkyl, lower-alkyl substituted by halogen, lower-alkyl substituted by hydroxy, cycloalkyl, cycloalkyl substituted by lower-alkyl, heterocyclyl or heteroaryl substituted by lower-alkyl.

11. The compound of claim 10, wherein $R^4$ is lower-alkyl, lower-alkyl substituted by hydroxy, cycloalkyl, tetrahydro-furanyl, tetrahydro-pyranyl or pyrazolyl substituted by lower-alkyl.

12. The compound of claim 11, wherein $R^4$ is isopropyl, 2-hydroxy-1-methyl-ethyl, (S)-2-hydroxy-1-methyl-ethyl, cyclopropyl, tetrahydro-furan-3-yl, tetrahydro-pyran-4-yl or 1-methyl-1H-pyrazol-4-yl.

13. The compound of claim 1, wherein $R^3$ and $R^4$, together with the nitrogen atom to which they are attached, form a heterocyclyl.

14. The compounds of claim 13, wherein $R^3$ and $R^4$, together with the nitrogen atom to which they are attached, form azetidin-1-yl or 1,1-dioxo-1,6-thiomorpholin-4-yl.

15. The compound of claim 1 selected from the group consisting of:
  N-Isopropyl-6-((5-methyl-3-propyl-isoxazol-4-yl)methoxy)-nicotinamide,
  6-((5-Methyl-3-propyl-isoxazol-4-yl)methoxy)-N-(tetrahydro-pyran-4-yl)-nicotinamide,
  N-Isopropyl-6-[(5-methyl-3-(3,3,3-trifluoro-propyl)-isoxazol-4-yl)methoxy]-nicotinamide,
  6-[(5-Methyl-3-(3,3,3-trifluoro-propyl)-isoxazol-4-yl)methoxy]-N-(tetrahydro-pyran-4-yl)-nicotinamide,
  6-((3-Butyl-5-methyl-isoxazol-4-yl)methoxy)-N-isopropyl-nicotinamide,
  6-((3-Butyl-5-methyl-isoxazol-4-yl)methoxy)-N-cyclopropyl-nicotinamide,
  6-((3-Butyl-5-methyl-isoxazol-4-yl)methoxy)-N-(tetrahydro-pyran-4-yl)-nicotinamide,
  6-((3-Butyl-5-methyl-isoxazol-4-yl)methoxy)-N-(2-hydroxy-1,1-dimethyl-ethyl)-nicotinamide,
  6-((3-Butyl-5-methyl-isoxazol-4-yl)methoxy)-N-(2-hydroxy-1-methyl-ethyl)-nicotinamide, and
  6-((3-Butyl-5-methyl-isoxazol-4-yl)methoxy)-N-(2-hydroxy-ethyl)-nicotinamide.

16. The compound of claim 1 selected from the group consisting of:
  6-((3-Butyl-5-methyl-isoxazol-4-yl)methoxy)-N—((R)-2-hydroxy-1-methyl-ethyl)-nicotinamide,
  6-((3-Butyl-5-methyl-isoxazol-4-yl)methoxy)-N—((S)-2-hydroxy-1-methyl-ethyl)-nicotinamide,
  6-((3-Butyl-5-methyl-isoxazol-4-yl)methoxy)-N-(2-hydroxy-2-methyl-propyl)-nicotinamide,
  6-((3-Butyl-5-methyl-isoxazol-4-yl)methoxy)-N-(tetrahydro-furan-3-yl)-nicotinamide,
  6-((3-Butyl-5-methyl-isoxazol-4-yl)methoxy)-N-(2-hydroxy-1-hydroxymethyl-ethyl)-nicotinamide,
  6-((3-Butyl-5-methyl-isoxazol-4-yl)methoxy)-N—(S)-tetrahydro-furan-3-yl-nicotinamide,
  6-((3-Butyl-5-methyl-isoxazol-4-yl)methoxy)-N-(2-hydroxy-propyl)-nicotinamide,
  [6-((3-Butyl-5-methyl-isoxazol-4-yl)methoxy)-pyridin-3-yl]-(1,1-dioxo-1,6-thiomorpholin-4-yl)-methanone,
  6-((3-Butyl-5-methyl-isoxazol-4-yl)methoxy)-N—((S)-2,2,2-trifluoro-1-methyl-ethyl)-nicotinamide,
  6-((3-Butyl-5-methyl-isoxazol-4-yl)methoxy)-N-(1-methyl-cyclopropyl)-nicotinamide, and
  Azetidin-1-yl-[6-((3-butyl-5-methyl-isoxazol-4-yl)methoxy)-pyridin-3-yl]-methanone,
or a pharmaceutically acceptable salt and ester thereof.

17. The compound of claim 1 selected from the group consisting of:
  6-((3-Butyl-5-methyl-isoxazol-4-yl)methoxy)-N-(1-methyl-1H-pyrazol-4-yl)-nicotinamide,
  6-((3-Butyl-5-methyl-isoxazol-4-yl)methoxy)-N-(1-methyl-1H-pyrazol-3-yl)-nicotinamide,
  6-((3-Butyl-isoxazol-4-yl)methoxy)-N-isopropyl-nicotinamide,
  6-((3-Butyl-isoxazol-4-yl)methoxy)-N-(2,2,2-trifluoro-ethyl)-nicotinamide,
  6-((3-Butyl-isoxazol-4-yl)methoxy)-N-(tetrahydro-pyran-4-yl)-nicotinamide,
  6-((3-Butyl-isoxazol-4-yl)methoxy)-N—((S)-2-hydroxy-1-methyl-ethyl)-nicotinamide,
  N-Isopropyl-6-[(5-methyl-3-(1-methyl-butyl)-isoxazol-4-yl)methoxy]-nicotinamide,
  6-((3-Cyclopentyl-5-methyl-isoxazol-4-yl)methoxy)-N-isopropyl-nicotinamide,
  6-((3-Cyclohexyl-5-methyl-isoxazol-4-yl)methoxy)-N-isopropyl-nicotinamide,
  6-((3-Cyclohexyl-5-methyl-isoxazol-4-yl)methoxy)-N-cyclopropyl-nicotinamide, and
  6-((3-Cyclohexyl-5-methyl-isoxazol-4-yl)methoxy)-N-(tetrahydro-pyran-4-yl)-nicotinamide,
or a pharmaceutically acceptable salt and ester thereof.

18. The compound of claim 1 selected from the group consisting of:
  6-((3-Cyclohexyl-5-methyl-isoxazol-4-yl)methoxy)-N-(2-hydroxy-ethyl)-nicotinamide,
  6-((3-Cyclohexyl-5-methyl-isoxazol-4-yl)methoxy)-N-(2-hydroxy-1,1-dimethyl-ethyl)-nicotinamide,
  6-((3-Cyclohexyl-5-methyl-isoxazol-4-yl)methoxy)-N-(2-hydroxy-1-methyl-ethyl)-nicotinamide,
  N-Isopropyl-6-[(5-methyl-3-(tetrahydro-pyran-4-yl)-isoxazol-4-yl)methoxy]-nicotinamide,
  N—((S)-2-Hydroxy-1-methyl-ethyl)-6-[(5-methyl-3-(tetrahydro-pyran-4-yl)-isoxazol-4-yl)methoxy]-nicotinamide,
  6-((3-Isobutoxy-5-methyl-isoxazol-4-yl)methoxy)-N-isopropyl-nicotinamide,
  N-Isopropyl-6-((5-methyl-3-pyrrolidin-1-yl-isoxazol-4-yl)methoxy)-nicotinamide,
  N-Isopropyl-6-((5-methyl-3-pyrrolidin-1-yl-isoxazol-4-yl)methoxy)-nicotinamide,
  6-[((3-Butyl-5-methyl-isoxazol-4-yl)methyl)-amino]-N-isopropyl-nicotinamide,
  6-[((3-Butyl-5-methyl-isoxazol-4-yl)methyl)-amino]-N-(2-hydroxy-1-methyl-ethyl)-nicotinamide, and
  6-[((3-Butyl-5-methyl-isoxazol-4-yl)methyl)-amino]-N-(tetrahydro-pyran-4-yl)-nicotinamide,
or a pharmaceutically acceptable salt and ester thereof.

19. The compound of claim 1 selected from the group consisting of:

6-((3-Butyl-5-methyl-isoxazol-4-yl)methoxy)-N-isopropyl-nicotinamide,
6-((3-Butyl-5-methyl-isoxazol-4-yl)methoxy)-N-(2-hydroxy-1-methyl-ethyl)-nicotinamide,
6-((3-Butyl-5-methyl-isoxazol-4-yl)methoxy)-N—((S)-2-hydroxy-1-methyl-ethyl)-nicotinamide,
6-((3-Butyl-5-methyl-isoxazol-4-yl)methoxy)-N-(tetrahydro-furan-3-yl)-nicotinamide,
6-((3-Butyl-5-methyl-isoxazol-4-yl)methoxy)-N-(1-methyl-1H-pyrazol-4-yl)-nicotinamide,
6-((3-Cyclohexyl-5-methyl-isoxazol-4-yl)methoxy)-N-isopropyl-nicotinamide,
6-((3-Cyclohexyl-5-methyl-isoxazol-4-yl)methoxy)-N-cyclopropyl-nicotinamide,
6-((3-Cyclohexyl-5-methyl-isoxazol-4-yl)methoxy)-N-(2-hydroxy-1-methyl-ethyl)-nicotinamide,
6-((3-Isobutoxy-5-methyl-isoxazol-4-yl)methoxy)-N-isopropyl-nicotinamide,
N-Isopropyl-6-((5-methyl-3-pyrrolidin-1-yl-isoxazol-4-yl)methoxy)-nicotinamide, and
N-Isopropyl-6-((5-methyl-3-pyrrolidin-1-yl-isoxazol-4-yl)methoxy)-nicotinamide,
or a pharmaceutically acceptable salt and ester thereof.

20. A pharmaceutical composition comprising a therapeutically effective amount of a compound of formula I

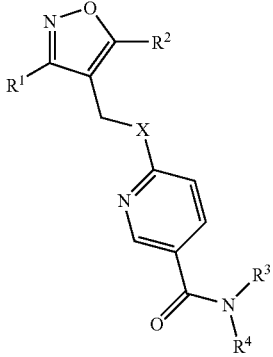

wherein

X is O or NH;

$R^1$ is a) lower-alkyl or lower-alkoxy, each optionally substituted with 1, 2, 3 or 4 substituents independently selected from the group consisting of halogen, cyano, hydroxy and lower-alkoxy, or b) cycloalkyl or heterocyclyl, each optionally substituted with 1, 2, 3 or 4 substituents independently selected from the group consisting of halogen, cyano, hydroxy, lower-alkyl and lower-alkoxy;

$R^2$ is hydrogen or lower-alkyl optionally substituted with 1, 2, 3 or 4 substituents independently selected from the group consisting of halogen, cyano and lower-alkoxy;

$R^3$ is hydrogen or lower-alkyl optionally substituted with 1, 2, 3 or 4 substituents independently selected from the group consisting of halogen, cyano, hydroxy and lower-alkoxy;

$R^4$ is lower-alkyl, cycloalkyl, heterocyclyl or heteroaryl, each optionally substituted with 1, 2, 3 or 4 substituents independently selected from the group consisting of halogen, cyano, hydroxy, oxo, lower alkyl and lower-alkoxy;

or wherein $R^3$ and $R^4$, together with the nitrogen atom to which they are attached, form a heterocyclyl, optionally substituted with 1, 2, 3 or 4 substituents independently selected from the group consisting of halogen, cyano, hydroxy, lower-alkyl, lower-alkoxy and oxo;

or a pharmaceutically acceptable salt and ester thereof and a pharmaceutically acceptable carrier.

* * * * *